(12) United States Patent
Tsuang et al.

(10) Patent No.: US 7,879,548 B2
(45) Date of Patent: Feb. 1, 2011

(54) DETECTION OF BIOMARKERS FOR NEUROPSYCHIATRIC DISORDERS

(75) Inventors: Ming T. Tsuang, La Jolla, CA (US); Ian P. Everall, San Diego, CA (US); Stephen J. Glatt, Liverpool, NY (US); William S. Kremen, Carlsbad, CA (US)

(73) Assignee: The Regents of the University of California, Oakland, CA (US)

( * ) Notice: Subject to any disclaimer, the term of this patent is extended or adjusted under 35 U.S.C. 154(b) by 366 days.

(21) Appl. No.: 11/884,400

(22) PCT Filed: Feb. 15, 2006

(86) PCT No.: PCT/US2006/005533

§ 371 (c)(1), (2), (4) Date: Jan. 11, 2008

(87) PCT Pub. No.: WO2006/089062

PCT Pub. Date: Aug. 24, 2006

(65) Prior Publication Data

US 2008/0261218 A1    Oct. 23, 2008

Related U.S. Application Data

(60) Provisional application No. 60/653,217, filed on Feb. 15, 2005.

(51) Int. Cl.
*A61K 49/00* (2006.01)
*C12Q 1/37* (2006.01)
*G01N 33/53* (2006.01)

(52) U.S. Cl. .............. 435/6; 435/7.1; 530/350
(58) Field of Classification Search .............. None
See application file for complete search history.

(56) References Cited

PUBLICATIONS

Steinau et al., J Mol Med., 82:750-755, Oct. 14, 2004.*
Chen et al., J Pathol., 202(3):321-329, Mar. 2004.*
Yang et al., Cancer Res., 58: 3150-3153, Jul. 1998.*
Huang et al., Int J Cancer, 118(10): 2433-2440, May 2006.*
Li et al., Mol. Nutr. Food Res., 52:1289-1299, 2008.*
Yao et al., J Psychiatric Res., 42: 639-643, 2008.*
Gladkevich, A., et al., "Lymphocytes as a neural probe: potential for studying psychiatric disorders", *Progress in Neuro-Psychopharmacology & Biological Psychiatry*, 28(3), (May 3, 2004),559-576.
Glatt, S. J., et al., "Comparative gene expression analysis of blood and brain provides concurrent validation of SELENBP1 up-regulation in schizophrenia", *Proceedings of the national academy of sciences of the United States of America*, 102(43), (Oct. 2005), 15533-15538.
Martin, K. J., et al., "High-sensitivity array analysis of gene expression for the early detection of disseminated breast tumor cells in peripheral blood", *Proceedings of the National Academy of Sciences*, 98(5), (Feb. 27, 2001),2646-2651.
Tsuang, M., et al., "Assessing the validity blood-based gene expression profiles for the classification of schizophrenia and bipolar disorder: A preliminary report", *American Journal of Medical Genetics*, 133B(1), (Feb. 5, 2005),1-5.
Vawter, M. P., et al., "Microarray screening of lymphocyte gene expression differences in a multiplex schizophrenia pedigree", *Schizophrenia research*, 67(1), (Mar. 1, 2004),41-52.
Kanazawa, T., et al., "The utility of SELENBP1 gene expression as a biomarker for major psychotic disorders: replication in schizophrenia and extension to bipolar disorder with psychosis.", *Am J Med Genet B Neuropsychiatr Genet.*, 147B(6), (Sep. 5, 2008), 686-9.

* cited by examiner

*Primary Examiner*—Lorraine Spector
*Assistant Examiner*—Stacey MacFarlane
(74) *Attorney, Agent, or Firm*—Schwegman, Lundberg & Woessner, P.A.

(57) ABSTRACT

Systems and methods provide a comprehensive high-throughput approach toward the sequential identification, prioritization, verification, and validation of etiologic factors in neuropsychiatric disorders, some of which can also be utilized as biomarkers for these illnesses. The systems and methods determine patterns of gene expression in various tissues from various samples under various experimental and non-experimental conditions, and uses the differences and similarities between the gene expression profiles observed under these conditions to delineate distinct gene expression profiles of risk and treatment of neuropsychiatric disorders.

7 Claims, 6 Drawing Sheets

DETECTION OF BIOMARKERS FOR NEUROPSYCHIATRIC DISORDERS

RELATED APPLICATION

This application is a U.S. National Stage filing under 35 U.S.C. 371 from International Application No. PCT/2006/005533 filed 15 Feb. 2006, published in English as WO 2006/089062 A2 on 24 Aug. 2006, which claims the benefit of U.S. Provisional Application Ser. No. 60/653,217 filed 15 Feb. 2005, which applications and publication are incorporated herein by reference.

FIELD

The embodiments of the present invention relate to detection of biomarkers and the use of biomarkers. More specifically, the embodiments relate to systems and methods for detecting biomarkers for neuropsychiatric disorders and the use of selenium binding protein 1 (SELENBP1) as a biomarker.

BACKGROUND

Neuropsychiatric disorders may be etiologically complex and heterogeneous thereby making it difficult to identify risk factors for a particular neuropsychiatric disorder. Microarray techniques hold great promise for identifying risk factors for neuropsychiatric disorders such as schizophrenia (SZ) but have not yet generated widely reproducible results due to methodological differences between studies and the high risk of type I inferential errors.

Schizophrenia has a substantial genetic basis, but its biological underpinnings remain largely unknown. Early attempts to profile the expression of specific neurochemicals in blood and postmortem brain tissue detected several promising candidate risk factors for SZ that ultimately could not be substantiated. Subsequent progress in mapping the human genome increased the viability of candidate gene association studies. Most candidate genes have been targeted based on their expression within systems widely implicated in the disorder (e.g., dopamine and glutamate neurotransmitter systems), and this approach may be used for clarifying the nature of dysfunction within these recognized candidate pathways; however, it may not be optimal for identifying additional novel risk factors outside of these systems.

The advent of microarrays that can survey the entire expressed human genome has made it possible to simultaneously investigate the roles of several thousand genes in a disorder. Relative to traditional candidate gene studies predicated on existing disease models, microarray analysis is a less-constrained strategy that may foster the discovery of novel risk genes that otherwise would not come under study. Because gene expression can reflect both genetic and environmental influences, it may be particularly useful for identifying risk factors for a complex disorder such as SZ, which is thought to have a multifactorial polygenic etiology in which many genes and environmental factors interact. However, the simultaneous consideration of thousands of dependent variables also increases the likelihood of false-positive results. In short, microarrays hold great promise for identifying etiologic factors for SZ but run the risk of being too liberal and failing to provide replicable results.

Several groups have characterized gene expression profiles of SZ in postmortem tissue from the dorsolateral prefrontal cortex (DLPFC) of the brain, which has been consistently identified as dysfunctional in the illness. These studies have noted variable patterns of dysregulated gene expression in several domains, including G protein signaling, metabolism, mitochondrial function, myelination, and neuronal development. However, not all of these studies have reported significant alterations in each domain. Methodological differences, including ethnic and demographic disparities, alternative microarray platforms, and diverse methods of data analysis, as well as the high risk of false positives, have been cited as factors possibly contributing to this variability.

As a result, the gene expression profiles generated by existing methods are prone to the identification of false-positive results or risk factors that have little utility for diagnostic and predictive purposes.

SUMMARY

The embodiments of the present invention include systems and methods providing a comprehensive high-throughput approach toward the sequential identification, prioritization, verification, and validation of etiologic factors in neuropsychiatric disorders, some of which can also be utilized as biomarkers for these illnesses. The systems and methods determine patterns of gene expression in various tissues from various samples under various experimental and non-experimental conditions, and uses the differences and similarities between the gene expression profiles observed under these conditions to delineate distinct gene expression profiles of risk and treatment of neuropsychiatric disorders.

DETAILED DESCRIPTION

In the following detailed description, reference is made to the accompanying drawings that form a part hereof, and in which is shown by way of illustration, specific embodiments in which the inventive subject matter may be practiced. These embodiments are described in sufficient detail to enable those skilled in the art to practice them, and it is to be understood that other embodiments may be utilized and that structural, logical, and electrical changes may be made without departing from the scope of the inventive subject matter. Such embodiments of the inventive subject matter may be referred to, individually and/or collectively, herein by the term "invention" merely for convenience and without intending to voluntarily limit the scope of this application to any single invention or inventive concept if more than one is in fact disclosed.

The following description is, therefore, not to be taken in a limited sense, and the scope of the inventive subject matter is defined by the appended claims.

In the Figures, the same reference number is used throughout to refer to an identical component which appears in multiple Figures. Signals and connections may be referred to by the same reference number or label, and the actual meaning will be clear from its use in the context of the description.

The functions or algorithms described herein are implemented in hardware, and/or software in embodiments. The software comprises computer executable instructions stored on computer readable media such as memory or other types of storage devices. The term "computer readable media" is also used to represent software-transmitted carrier waves. Further, such functions correspond to modules, which are software, hardware, firmware, or any combination thereof. Multiple functions are performed in one or more modules as desired, and the embodiments described are merely examples. A digital signal processor, ASIC, microprocessor, or any other type of processor operating on a system, such as a personal computer, server, a router, or any other device capable of processing data including network interconnection devices executes the software.

Some embodiments implement the functions in two or more specific interconnected hardware modules or devices with related control and data signals communicated between and through the modules, or as portions of an application-specific integrated circuit. Thus, the example process flow is applicable to software, firmware, and hardware implementations.

Specific ranges, values, and embodiments provided below are for illustration purposes only and do not otherwise limit the scope of the invention, as defined by the claims.

As used herein, "selenium binding protein" includes polypeptides having at least 80%, e.g., at least 85%, 90%, 95%, or more amino acid sequence identity to sequences having NCBI Accession Nos. CAG33133, CAH70328, AAH32997, Q13228, P17563, AAH11202, NP003935, NP 033176, AAH74008, NP956864, NP543168, AAX43635, AAX31965, AAH56590, or AAH09084, and nucleic acid sequence encoding those polypeptides. In one embodiment, the selenium binding protein is selenium binding protein-1, e.g., human, rodent, for instance, rabbit, mouse, rat, mink or guinea pig, or nonhuman primate selenium binding protein-1.

Figure 1:
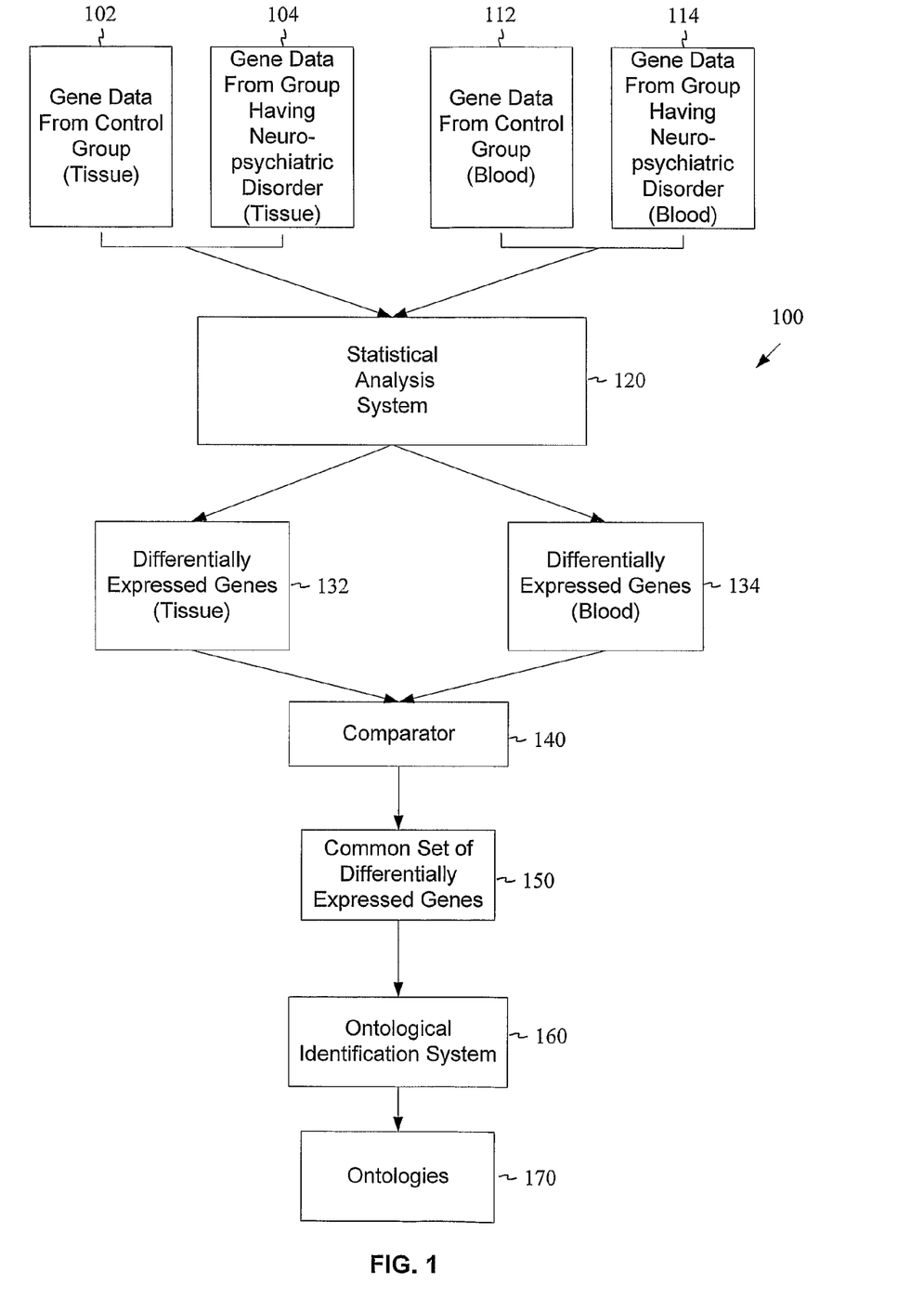
FIG. 1 illustrates the major components of a system for detecting biomarkers for neuropsychiatric disorders according to embodiments of the invention.

FIG. 1 illustrates a system 100 for detecting potential biomarkers according to embodiments of the invention. In some embodiments, system 100 includes a statistical analysis system 120, a comparator 140, and an ontological identification system 160. In some embodiments, statistical analysis system 120 is a computerized system that receives two input files each of which contain gene expression data, performs a statistical analysis of the two files, and generates an output file that contains gene data representing genes that are differentially expressed between the two input files. In general, one of the input files (e.g. file 102 or 112) contains gene expression data for a control group not having a neuropsychiatric disorder of interest and the other input file (e.g. file 104 or 114) contains gene expression data for a group that has been diagnosed with the neuropsychiatric disorder of interest. Further, the input files generally contain gene expression data obtained from the same source type in the control group and the sample group. For example, the gene expression data may be obtained from central nervous system tissue from the control group and the sample group or from blood samples obtained from the control group and the sample group.

Statistical analysis system 120 in some embodiments uses a model that assumes multiplicative rather than additive noise. Additionally, in some embodiments, statistical analysis system may be designed to eliminate statistically significant outliers. Additionally, the statistical model used in some embodiments assumes a uniform background level that is estimated from both mismatch and perfect-match probe intensities. As noted above, the output of statistical analysis system 120 is a file containing gene data for differentially expressed genes in the two input files.

In particular embodiments, statistical analysis system 120 is the CORGON biostatistical analysis system. Further details on the operation of the CORGON biostatistical analysis system is found in Sasik, R., Calvo, E. & Corbeil, J. "Statistical Analysis of High-Density Oligonucleotide Arrays: A Multiplicative Noise Model" *Bioinformatics* 18, 1633-1640 (2002), which is hereby incorporated by reference.

Additionally, some embodiments employ an algorithm in which identification of differentially expressed genes is based on their statistical significance beyond a threshold of P=0.05. In these embodiments, the P value of each gene is determined by two-tailed unadjusted permutation testing of 100,000 permutations of sample labels for each gene. For each permutation, the t statistic was calculated from log(expression) values, and the P value was estimated as the fraction of permutations for which the absolute value of the t statistic was greater than or equal to the absolute value of the unpermuted t statistic. In particular embodiments, an implementation of a FOCUS algorithm is used. Further details on the FOCUS algorithm may be found in Cole, S. W., Galic, Z. & Zack, J. A. "Controlling false-negative errors in microarray differential expression analysis: a PRIM approach" (2003) *Bioinformatics* 19, 1808-1816.

The application of the FOCUS algorithm in conjunction with the statistical model used in some embodiments described above may be useful in reducing the occurrence of Type I errors (false positives).

In operation, to determine biomarkers for a neuropsychiatric disorder of interest, statistical analysis system 120 is executed twice, once for each of two sample types, central nervous system tissue and blood. Thus in one execution, an input file 102 having gene expression data from central nervous system tissue samples obtained from a control group and a second input file 104 having gene expression data from central nervous system tissue samples obtained from individuals having the neuropsychiatric disorder are supplied to the statistical analysis system 120 to produce output file 132 having differentially expressed gene data in the brain tissue samples of the two input groups. In some embodiments, input files 102 and 112 may be cell intensity (CEL) files from the National Brain databank (NBD) web site.

Various forms of central nervous system tissue may be used. In some embodiments, DLPFC tissue may be used. In alternative embodiments, other tissue samples from other brain regions may be used to obtain gene expression data. In further alternative embodiments, cerebrospinal fluid may be used to obtain gene expression data. The embodiments of the invention are not limited to a particular central nervous system component.

In a second execution, statistical analysis system 120 receives an input file 112 having gene expression data from blood samples obtained from a control group not having the neuropsychiatric disorder and a second input file 114 having gene expression data from blood samples obtained from individuals having the neuropsychiatric disorder and produces an output file 134 having differentially expressed gene data in the blood samples of the two input groups. In some embodiments, the blood samples comprise peripheral blood cells.

Comparator 140 comprises software that compares two files having differentially expressed gene data and produces an output file 150 comprising a set of differentially expressed gene data that is common in both the brain tissue samples and the blood samples. In some embodiments, the comparator software may be a spreadsheet style program that sorts and orders entries in order to perform a comparison. An example of such a program is the Microsoft Excel spreadsheet program available from Microsoft Corporation of Redmond Wash.

Ontological identification system 160 receives the common set of differentially expressed gene data 150 and applies a bioinformatic analysis algorithm to identify the ontologies (biological processes, molecular functions, and cellular components) linked to those genes. In some embodiments, the identified genes are placed in an output 170 using standardized gene ontology (GO) terms, such as terms recognized by the GO Consortium and defined in "Gene Ontology: tool for the unification of biology. The Gene Ontology Consortium (2000) Nature Genet. 25: 25-29. In some embodiments, Ontological identification system 160 compares the list of differentially expressed genes identified by the statistical analysis system 120 and comparator 140 with the list of all genes on a microarray and determines which of the standardized GO terms are more frequently represented than would be expected by chance based on the genes represented in the entire microarray. Further, in some embodiments, ontological identification system 160 calculates conditional P values, which allows for the discovery of significant terms even if they are small in size.

In particular embodiments, ontological identification system 160 comprises an implementation of the MicroArray Data Characterization and Profiling (MADCAP) algorithm. Further details on the MADCAP algorithm may be found in Lozach, J., Sasik, R., Ogawa, S., Glass, C. K. "MADCAP: MicroArray Data Characterization And Profiling. A tool for profiling lists of genes with different expression patterns" (2003) in European Conference on Computational Biology (Institut National de la Recherche Agronomique, Paris), p. GE24, which is hereby incorporated by reference.

Figure 2:
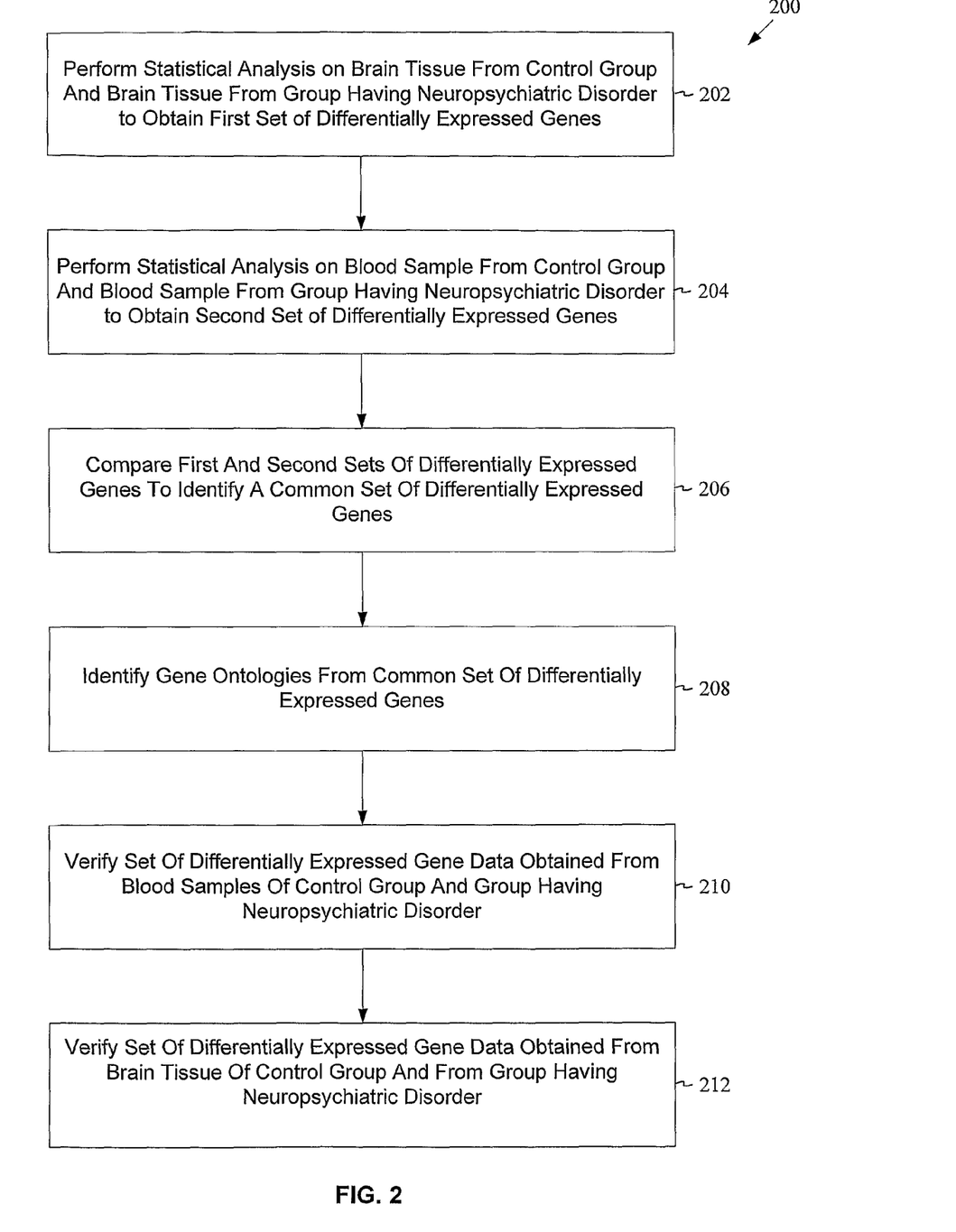
FIG. 2 is a flowchart illustrating an exemplary method for detecting biomarkers for neuropsychiatric disorders according to embodiments of the invention.

Further details on the operation of the system described above will be described below with reference to FIG. 2. FIG. 2 illustrates flow diagrams of methods for determining biomarkers for neuropsychiatric disorders. The methods to be performed by the operating environment may include computer programs made up of computer-executable instructions. Describing the methods by reference to a flowchart enables one skilled in the art to develop such programs including such instructions to carry out the methods on suitable computers (the processor or processors of the computer executing the instructions from computer-readable media such as ROMs, RAMs, hard drives, CD-ROM, DVD-ROM, flash memory etc. The methods illustrated in FIG. 2 are inclusive of acts that may be taken by an operating environment executing an example embodiment of the invention. In the discussion below, nonlimiting examples of the execution of the method may be provided in order to provide further description of the method.

The method begins by performing statistical analysis on gene expression data obtained from brain tissue from a control group and from brain tissue from a group having a neuropsychiatric disorder to obtain a first set of differentially expressed genes (block 202). In some embodiments, the brain tissue may be DLPFC, however the embodiments are not limited to a particular type of brain tissue.

In particular embodiments, gene expression data were obtained from cRNA microarrays of fresh-frozen postmortem DLPFC tissue samples (50 mg) from 19 SZ patients and 27 nonpsychiatric control subjects in the National Brain Databank (NBD) maintained by the Harvard Brain Tissue Resource Center (HBTRC). Patients and controls were closely matched on gender (68% vs. 70% male; P=0.887) and mean age (57 vs. 56 yrs; P=0.955), and DLPFC samples were very similar in laterality (58% vs. 52% right hemisphere; P=0.875), mean pH (6.4 vs. 6.4; P=0.981), and mean postmortem interval (21 vs. 20 h; P=0.739). Ascertainment and diagnosis of these subjects according to *Diagnostic and Statistical Manual of Mental Disorders* (DSM-IV) criteria, preparation of brain tissue, extraction, purification and hybridization of RNA, quantification of expression levels on cRNA microarrays, and quality-control procedures were all performed at the Harvard Brain Tissue Resource Center by standard methods.

At the Harvard Brain Tissue Resource Center, ≈50 mg of fresh frozen brain tissue was obtained from the DLPFC of each subject, and RNA was extracted using a Totally RNA Kit (Ambion, Austin, Tex.). RNA samples were then purified using an RNeasy Kit (Qiagen, Valencia, Calif.). RNA quality of each sample was verified before hybridization by examining the state of 28S and 18S ribosomal RNA by gel electrophoresis on an Agilent 2100 bioanalyzer (Agilent Technologies, Palo Alto, Calif.). RNA quality was very similar between samples from SZ patients and control subjects, as determined by several indices, including the mean 28S:18S RNA ratio (1.11 vs. 1.07; P=0.790) and the mean 3':5' ratio of the RNA transcripts of the housekeeping genes G3PDH (1.57 vs. 1.44; P=0.407) and ACTB (2.42 vs. 2.33; P=0.728).

Each purified and quality-assured RNA sample (8 µg) was reverse-transcribed by using a SuperScript II double-stranded cDNA synthesis kit (Invitrogen) to yield complimentary cDNAs, which were then transcribed and amplified in vitro with an Enzo-IVT kit (Affymetrix) to yield biotin-labeled cRNAs of all mRNAs present in the brain tissue sample. Samples of cRNA were then fragmented and hybridized to a GeneChip Human Genome U95A or U133A array (Affymetrix), which was stained in a GeneChip Fluidics Station 400 (Affymetrix) and scanned twice in a DNA Microarray Scanner 2500 (Agilent Technologies). Scans were then visually inspected for artifacts such as edge effects or scratches, which were detected in <5% of samples. Samples affected with such artifacts were removed from the National Brain Databank (NBD) database.

Microarray suite 5.0 software (Affymetrix) was then used to assess the quality of the scans. For arrays with a rate of probe detection below 35%, the entire experimental procedure was repeated from the RNA extraction step forward. If the rate of probe detection was not improved above 35%, the gene expression data for that sample was not added to the NBD database. The rates of probe detection for the samples that we obtained from the NBD were essentially equivalent between the group of schizophrenia (SZ) patients and control subjects (45.8 vs. 45.9% present; P=0.913), and no sample had a rate of probe detection below 35%.

In some embodiments, expression levels of all genes identified as differentially expressed by the statistical analysis may then be examined in relation to antipsychotic and other medication use to determine whether the elevated frequency of such exposures among patients may account for group differences in gene expression.

The effects of anticonvulsant, antidepressant, and anxiolytic medications may be examined by comparing gene expression levels observed in treated and untreated groups with t tests for independent samples. Advancing beyond this scheme, antipsychotic medications may be evaluated in a more quantitative manner by converting daily dosages to a common metric (e.g., maximum effective dose) and examining correlations between this daily dose index and the expression level of each differentially expressed gene. Highly conservative family-wise corrections for multiple testing within each medication class may performed by using the Bonferroni correction Additionally, a system executing the method performs statistical analysis on gene expression data obtained from blood samples from a control group and from blood samples from a group having the neuropsychiatric disorder to obtain a second set of differentially expressed genes (block 204).

In the execution of an embodiment, peripheral whole-blood samples (10 ml) were obtained from a separate set of 30 SZ patients and 24 nonpsychiatric control subjects. Patients and controls were of similar gender (40% vs. 58% male; P=0.180) but differed in mean age (34 vs. 42 yrs; P=0.014). All blood samples were collected into sterile violet-capped Vacutainer tubes (Becton Dickinson) containing $K_3$ EDTA, temporarily stored at 4° C., and processed within 6 h of collection. Ascertainment and diagnosis of these subjects according to *Diagnostic and Statistical Manual of Mental Disorders* (DSM-IV, ref. 12) criteria; collection and preparation of blood samples; separation and lysis of peripheral blood cells (PBCs); extraction, purification, and hybridization of RNA; quantification of expression levels on cRNA microarrays; and quality-control procedures were all performed by standard methods.

For some embodiments, each sample was processed by separating plasma, buffy coat, and red blood cell layers through centrifugation. Plasma was discarded, red blood cells were ruptured with lysis buffer, and each mixture was centrifuged again, yielding a pellet of white blood cells, which was briefly washed in lysis buffer. TRIzol (1 ml; Invitrogen) was then applied to extract mRNA, which was then purified and assessed for quality as described above for DLPFC samples.

Each purified and quality-assured RNA sample (5 µg) was prepared for microarray, hybridized to either a GeneChip Human Genome U133A or U133 Plus 2.0 array, and scanned once using an Affymetrix GeneChip Scanner and Affymetrix gcos software, Ver. 1.1.1, according to the manufacturer's published protocols (Affymetrix).

The gene expression data for the blood samples may then be analyzed by statistical analysis system 160 as described above an in a manner similar to that of the brain tissue samples.

The system also compares first and second sets of differentially expressed genes to identify a common set of differentially expressed genes (block 206). For example, the list of genes differentially expressed in the blood of these patients and controls may be compared with the list of genes previously identified as differentially expressed in the DLPFC of SZ patients and controls in the NBD. Medication effects on gene expression levels may be examined as outlined above for DLPFC samples, and the effect of age (which differed between patients and controls) may be evaluated by correlation as well.

Next, the system identifies gene ontologies from the common set of differentially expressed genes (block 208). In some embodiments, this may be performed by an ontological identification system 160, including systems using the MADCAP algorithm. MADCAP compares the list of differentially expressed genes identified by statistical analysis system with the list of all genes on a microarray and determines which of the standardized GO terms are more frequently represented than would be expected by chance based on the genes represented in the entire microarray.

In some embodiments, genes may be classified according to the standardized ontology terms recognized by the Gene Ontology Consortium (GOC). The gene ontology (GO) classification system established and maintained by the GOC describes gene products in three domains, including Biological Process, Cellular Component, and Molecular Function. The grouping of genes based on ontological dimensions further increases the likelihood of identifying true-positive results for genes that exist within and influence the activity of a family of functionally related genes or an extended gene system that may change in synchrony in the disease state.

Ontological classifications and relationships of genes may be analyzed with the MicroArray Data Characterization and Profiling (MADCAP) algorithm, which is a tool for unsupervised statistical analysis of gene lists under the three separate GOs of the GOC. The algorithm finds all statistically significant ontology "terms" (of the >18,000 terms recognized by the GOC) and the genes that represent them, and creates a graphical output of the ontology highlighting significant terms (e.g. see FIGS. 4A and 4B). The input into MADCAP consists of two lists of genes: a reference list and a selected list. The reference list typically contains all genes detected as expressed in the corgon-analyzed microarray dataset. The selected list of genes represents a smaller group of genes selected from the reference list according to some criterion, in some embodiments, the genes that were identified by the statistical analysis system as significantly differentially expressed in the DLPFC of SZ patients and control subjects. MADCAP then identifies which, if any, biological processes, cellular components, and molecular functions are significantly represented in the selected set of genes. Each gene can be linked to several ontology terms, either directly or through daughter GO terms. The reference gene list defines a reference ontology graph as determined by connections of individual genes to ontology terms and connections of terms to other terms. The selected genes define a subgraph of the reference graph. To identify the biological processes represented by the selected genes, MADCAP searches for terms linked to an unusually high number of selected genes. Specifically, starting from the root term of the subgraph and using the known structure of the graphs, we calculate the probability for each immediate daughter term (a value) that it be linked to as many or more selected genes than if the same number of genes was selected from the reference list at random. If the selected genes had been selected by a specific biological process (or processes) rather than at random, the process itself can be detected by an unusually large number of selected genes.

In some embodiments, the method includes verifying the set of differentially expressed gene data obtained from blood samples of the control group and the group having the neuropsychiatric disorder (block 210).

In the execution of a particular embodiment, the level of mRNA expression of the strongest candidate biomarker gene (SELENBP1, which was significantly up-regulated in both DLPFC and PBCs in SZ) was quantified in PBCs by RT-PCR. Total blood RNA isolated by the TRIzol method was reversed-transcribed into single-stranded cDNA by using a High-Capacity cDNA Archive Kit (Applied Biosystems) in a 100-µl reaction. Each sample of cDNA (2 ng) was then mixed with SYBR green master mix (Qiagen, Valencia, Calif.) and primers in a 20-µl reaction. Forward and reverse primers were designed by using PRIMERQUEST (Integrated DNA Technologies, Coralville, Iowa). PCR amplification was performed by using DNA Engine Opticon (MJ Research, Cambridge, Mass.). An automatically calculated melting point dissociation curve was examined to ensure specific PCR amplification and the lack of primer-dimer formation in each well. The comparative $C_t$ equation (Applied Biosystems) was used to calculate relative fold changes between patient and control samples. Briefly, gene expression levels were represented as $2_t^{-D\Delta C}$, where $D\Delta C_t=\{[\Delta C_t(\text{single sample})]-[\text{mean }\Delta C_t(\text{control samples})]\}$, $\Delta C_t=\{[C_t(\text{target gene})]-[C_t(\text{ACTB})]\}$, and ACTB is the housekeeping gene coding for β actin.

In some embodiments, the method includes verifying the set of differentially expressed gene data obtained from the brain tissue of the control group and from the group having the neuropsychiatric disorder (block 212). In some embodiments, the verification include analyzing immunohistochemistry for the sample.

In the execution of a particular embodiment, paraffin wax-embedded DLPFC brain tissue sections (10 μm) were treated with citrate buffer, microwaved for 10 min, and exposed for 24 h at 4° C. to the mouse antiselenium binding protein monoclonal antibody (1:250 dilution; MBL International, Woburn, Mass.). Antibody was detected by using the mouse monoclonal Vectastain ABC kit and the 3,3' diaminobenzidine substrate for peroxidase (Vector Laboratories). Sections were counterstained with hematoxylin, visualized on a Zeiss microscope, and analyzed by using IMAGE-PRO PLUS software (Media Cybernetics, Silver Spring, Md.).

Results of the Execution of Particular Embodiments

Gene Expression in DLPFC. Application of the CORGON and Focus algorithms described above to the brain gene expression data from 19 SZ patients and 27 control subjects in the NBD identified 177 genes that were differentially expressed in the DLPFC of the two groups. Of these, 111 genes were up-regulated, and 66 were down-regulated in SZ. The Affymetrix probe number, accession number, gene symbol, gene product, and chromosomal locus of each differentially expressed gene, as well as its fold-change difference in expression between SZ patients and control subjects and the corresponding P value, are provided in Table 4 below. Anticonvulsant-treated subjects showed significant down-regulation of six genes and up-regulation of one gene relative to untreated subjects, whereas anxiolytic treatment increased the expression of two genes and decreased the expression of two others. Antidepressant treatment influenced the expression of many more genes, with 10 showing significant upregulation and 7 showing significant down-regulation with treatment. Daily dosage of antipsychotic medication had a significant positive impact on the expression of 13 genes but was not significantly related to down-regulation of any genes. The significance of all of these medication effects was abolished by Bonferroni correction for multiple testing.

Figure 4A:
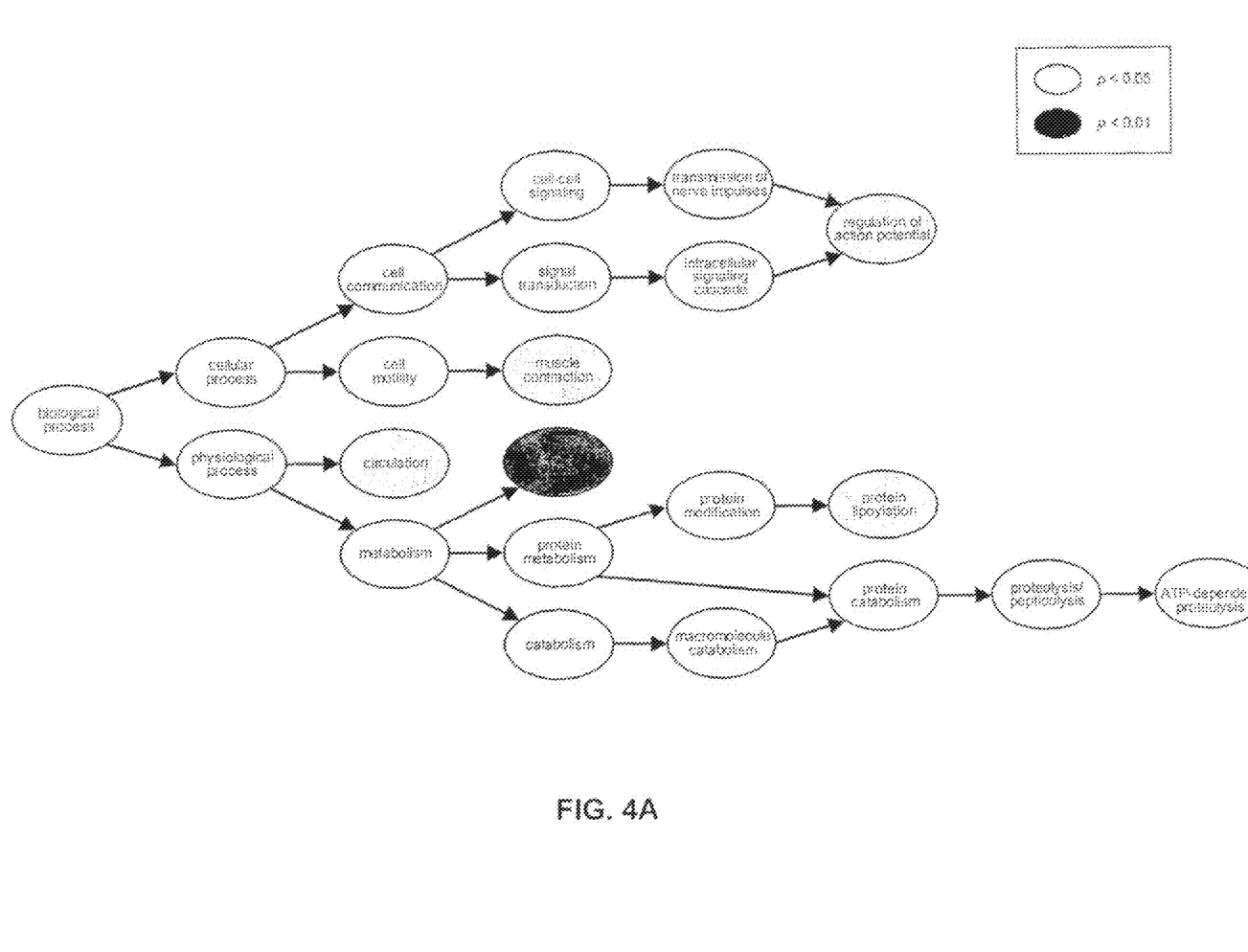
FIGS. 4A and 4B are graphs illustrating relationships between ontology terms identified by embodiments of the invention as overrepresented among genes differentially expressed in DLFPC in SZ.
Figure 4B:
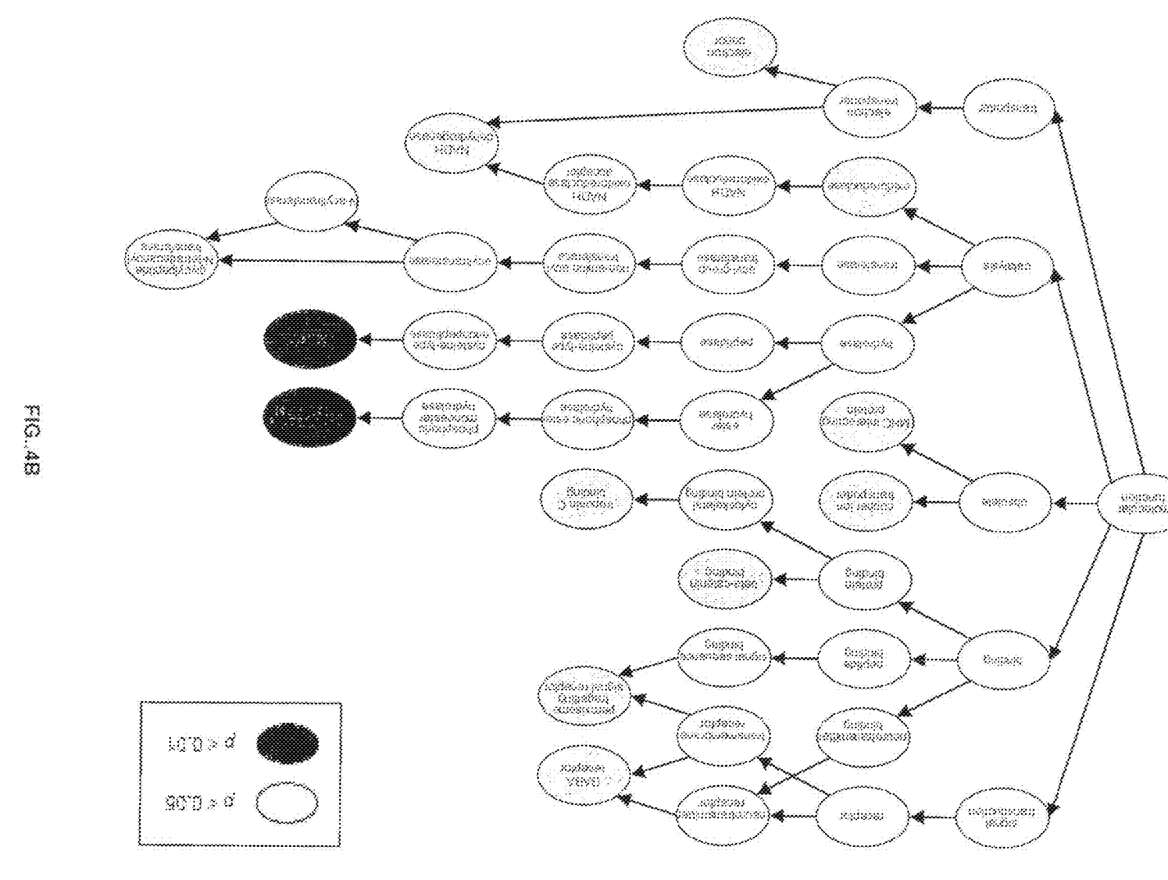

The 177 differentially expressed genes were then profiled by MicroArray Data Characterization and Profiling, and 25 were found to be linked to one or more overrepresented ontologies. Thirteen of the 25 genes represented six Biological Process GO terms. FIG. 4A is a graph showing the relationships between biological process ontology terms identified as overrepresented among genes differentially expressed in DLPFC in SZ. The most populated term within this ontology was Energy Pathways (P=0.007), which described the involvement of six genes shown in Table 1 below. In addition, 12 Molecular Function GO terms were represented by 18 genes. FIG. 4B is a graph showing the relationships between molecular function ontology terms identified as overrepresented among genes differentially expressed in DLPFC in SZ. The most populated term in this ontology was oxidoreductase activity (P=0.031), which described the function of seven genes and which are shown in Table 2 below. Three of these genes (NDUFA2, NDUFB5, and NDUFC1) were also classified as having NADH dehydrogenase activity. Genes representing terms in both the Biological Process and Molecular Function ontologies included ACOX1, COX7C, COX17, CNN3, NDUFA2, and NMT1, of which three genes (ACOX1, COX7C, and NDUFA2) had oxidoreductase activity within energy pathways. The remaining 152 differentially expressed genes were linked to GO terms that were not significantly overrepresented.

Gene Expression in PBCs. Application of the CORGON and Focus algorithms to the gene expression data from a separate sample of 30 SZ patients and 24 control subjects from Taiwan identified 123 genes that were differentially expressed in PBCs from the two groups. Of these, 67 genes were up-regulated and 56 down-regulated in SZ. The Affymetrix probe number, accession number, gene symbol, gene product, and chromosomal locus of each differentially expressed gene, as well as its fold-change difference in expression between SZ patients and control subjects and the corresponding P value, are provided in Table 5 below. Eight genes increased and 10 genes decreased significantly in expression level with age. Anticonvulsant-treated subjects differed from untreated subjects in the expression of only one gene, which was up-regulated; however, antidepressant treatment was associated with significant up-regulation of 15 genes and significant down-regulation of two others. The effects of age and these classes of medication did not remain significant after correction for multiple testing. Remarkably, anxiolytic treatment was associated with significant upregulation of 34 genes and down-regulation of another 40. Differential expression of 12 of these genes [including CSDA, EPB42, FBXO9, FKBP8, GSK3A HBA1 (two transcripts), HBA2, HBB (two transcripts), HLA-B, and UBB) remained significant after correcting for multiple testing. Daily dosage of antipsychotic medication was linearly related to the expression of only one gene (G0S2), which also remained statistically significant after corrections for multiple testing were applied.

Comparing the list of 123 genes differentially expressed in PBCs with that obtained from DLPFC identified six genes common to both. These six genes are detailed in Table 3 below. BTG1, HRNPA3, and SFRS1 were significantly up-regulated in the DLPFC in SZ but significantly down-regulated in PBCs from the other sample of SZ patients; the reverse pattern of differential expression was observed for GSK3A, which was the only one of these six genes to show a significant relationship to psychotropic medication (i.e., anticonvulsant) use. In contrast, SELENBP1 was significantly up-regulated in both tissues from the two samples of SZ patients. HLA-DRB1 was significantly downregulated in both DLPFC and PBCs in SZ; however, different probe sets (corresponding to different transcripts of the same gene) were associated with the illness in the two tissues.

SELENBP1 was identified as the strongest candidate biomarker among all genes differentially expressed in SZ, because it was the only gene for which identical probe sets indicated significant differential expression in a similar direction in both brain and blood in SZ. This significant up-regulation was substantiated by RT-PCR in PBCs from a randomly selected subset of the same SZ patients (n=21) and controls (n=18) that were profiled by microarray analysis. A highly significant (P=0.003) 2.2-fold increase in SELENBP1 was observed in PBCs of SZ patients by RT-PCR, which closely corresponded to the significant 2.0-fold up-regulation of the gene observed by microarray.

Figure 3A:
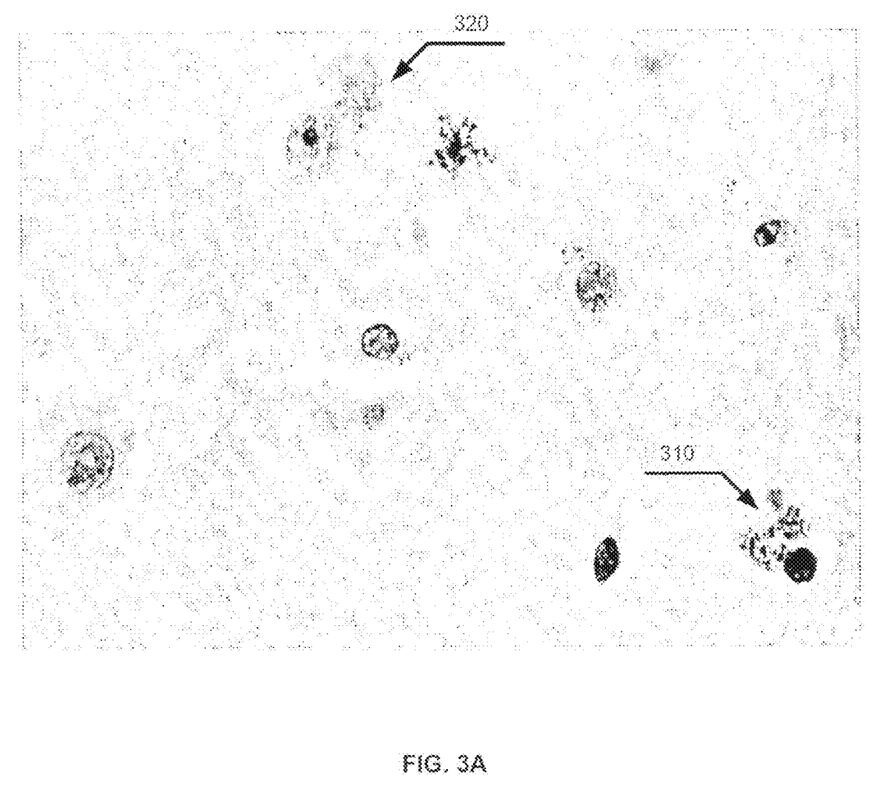
FIGS. 3A and 3B illustrate the expression of SELENBP1 protein in DLPFC of a control subject and a patient diagnosed with schizophrenia.
Figure 3B:
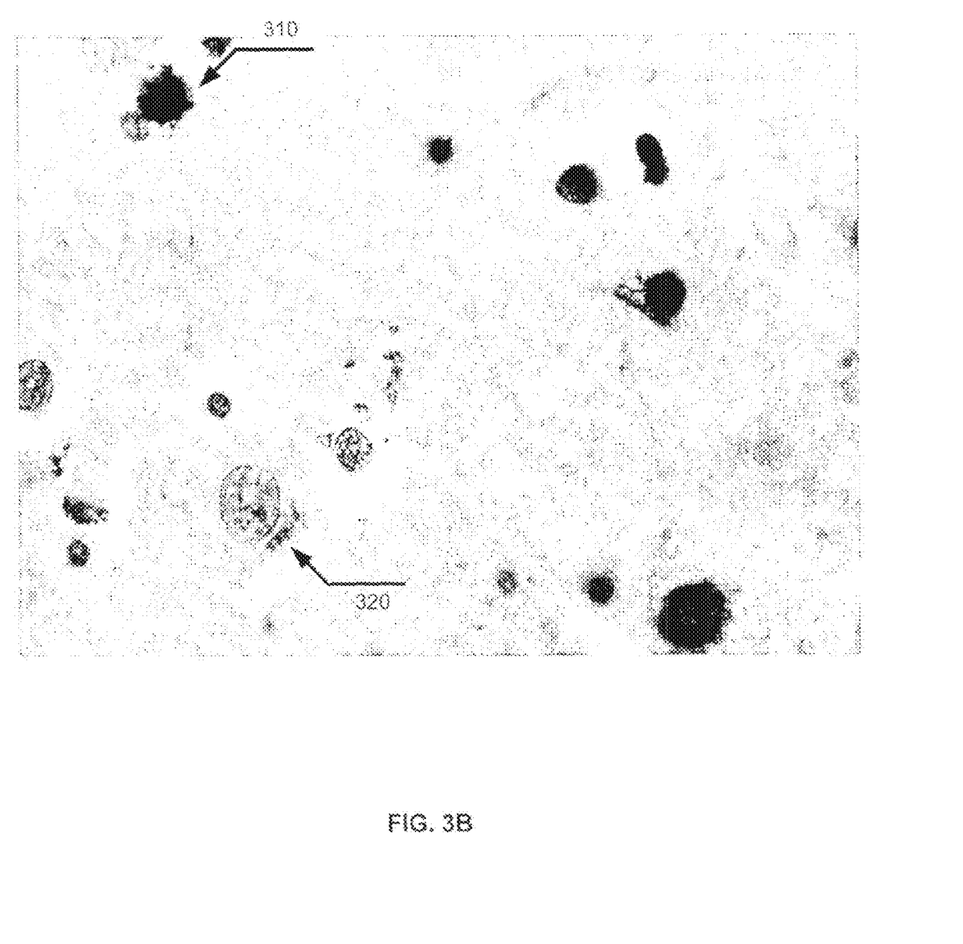

Protein Expression in DLPFC. Granular cytoplasmic staining of SELENBP1 protein was observed in a proportion of neurons and glia in DLPFC tissue from each of the four control subjects and four SZ patients. A representative example of the antibody-staining pattern observed in controls is shown in FIG. 3A, whereas a representative example of the antibody-staining pattern observed in patients is shown in FIG. 3B. Arrows 310 and 320 indicate antibody staining of cytoplasm in different cell types, with arrow 310 indicating glia and arrow 320 indicating neurons. Compared with control tissue, the intensity and ratio of glial/neuronal SELENBP1 antibody staining was noticeably increased in DLPFC tissue from at least three of the four SZ patients. The enhanced intraglial staining of SELENBP1 antibody in samples from SZ patients was most notable in a perinuclear rim of increased expression. No staining was observed in any cell when the primary antibody was omitted.

Analysis of Results

In some embodiments, a protocol for analysis and interpretation of gene expression microarray data includes using the CORGON and Focus algorithms to limit type I errors and MicroArray Data Characterization and Profiling to identify the ontologies represented by differentially expressed genes. Application of embodiments to gene expression data from DLPFC in SZ identified 177 genes, 6 biological processes, and 12 molecular functions that may be considered as high-priority targets for gene association analyses and hypothesis-driven functional studies. Twenty-eight of these genes also code to chromosomal loci strongly implicated in SZ by linkage analysis (Table 4) and are thus particularly attractive candidates. These include four genes (ACOX1, NDUFA2, SUCLG1, and TAPBP) that were also linked to significantly overrepresented GO terms, and SFRS1 and HLA-DRB1, which were differentially expressed in both DLPFC and PBCs in SZ. These genes provide reference points for the fine-mapping and positional cloning of putative SZ risk loci.

Application of embodiments of the invention resulted in GO terms overrepresented in DLPFC in the present study that were generally related to neurotransmitter systems not typically implicated in SZ (e.g., GABA receptor activity), neuronal processes not specific to a given neurotransmitter system (e.g., regulation of action potential), or biological processes not specific to the nervous system (e.g., energy pathways). More precisely, genes related to energy metabolism were predominant among those differentially expressed in DLPFC in SZ. Furthermore, at least four of the genes implicated in the results described above are involved in electron transfer, and three of these are also part of the NADH dehydrogenase complex located in the inner mitochondrial membrane. These data suggest that dysfunction within particular pathways or processes, but perhaps not necessarily in specific genes, might be important in the etiology of SZ.

Additionally, each of the 177 genes differentially expressed in DLPFC of SZ patients is a promising candidate risk gene. Also, the 123 genes differentially expressed in PBCs from such patients can be considered putative biomarkers for the illness. Six of the putative biomarker genes identified above in PBCs were also differentially expressed in the brain in SZ. Among these were BTG1, which regulates cell proliferation, and three genes (GSK3A, HNRPA3, and SFRS1) that regulate RNA splicing or transcription. The genes noted above may be considered secondary candidate SZ biomarkers to SELENBP1 and HLADRB1, which showed altered expression in the same direction in both DLPFC and PBCs (up- and down-regulation, respectively). Furthermore, HLA-DRB1 maps to the MHC region on chromosome 6p21.3, which is a prime candidate locus for SZ (22), and SELENBP1 maps to chromosome 1q21-22, a locus that has been strongly linked to SZ in some but not most genome-wide linkage studies.

Additionally, the utility of SELENBP1 as a potential peripheral biomarker was substantiated by RT-PCR verification of its up-regulation in PBCs. The altered levels of SELENBP1 transcripts measured in DLPFC and PBCs also translated into observable consequences at the functional level, because analyses suggests that expression of SELENBP1 protein was denser in glia and less dense in neurons of the DLPFC in SZ.

Thus various embodiments of the invention use SELENBP1 in various methods. For example, in some embodiments, a method to diagnose a neuropsychiatric disorder comprises detecting or determining the amount or level of selenium binding protein expression in cells in a physiological sample of a first mammal. An increase in the amount or level of selenium binding protein expression in the cells of the first mammal relative to the amount of level of selenium binding protein expression in cells of a mammal not having a psychotic mental disorder is indicative of a psychotic mental disorder in the first mammal. The physiological sample may be blood, including peripheral blood cells.

In further embodiments, a method to determine a mammal at risk of a neuropsychiatric disorder includes comparing the amount or level of selenium binding protein expression in cells in a physiological sample from a first mammal to the amount or level of selenium binding protein expression in cells from the first mammal at an earlier point in time or to the amount or level of selenium binding protein expression in cells of a mammal not having a neuropsychiatric disorder. An increase in the amount or level of selenium binding protein expression in the cells of the first mammal over time or relative to the mammal not having a neuropsychiatric disorder is indicative that the first mammal is at risk of a neuropsychiatric disorder. The physiological sample may be blood, including peripheral blood cells.

In still further embodiments, a method to determine the risk of progression of a neuropsychiatric disorder in a mammal includes comparing the amount or level of selenium binding protein expression in cells in a physiological sample from a mammal having a neuropsychiatric disorder to the amount or level of selenium binding protein expression in cells from the mammal at an earlier point in time. An increase in the amount or level of selenium binding protein expression over time is indicative that the mammal is at risk of progression of the neuropsychiatric disorder. The physiological sample may be blood, including peripheral blood cells.

In yet further embodiments, a method to determine whether an agent inhibits selenium binding protein expression in cells of a mammal includes a) administering an agent to a mammal; and b) detecting or determining whether the agent inhibits selenium binding protein expression in cells in a physiological sample of the mammal.

In further embodiments, a method to determine whether an agent inhibits or treats a neuropsychiatric disorder includes:

a) administering an agent to a mammal having a neuropsychiatric disorder; and b) detecting or determining whether the agent inhibits selenium binding protein expression in cells in a physiological sample of the mammal. A decrease in the amount or level of selenium binding protein expression in the cells is indicative of an agent useful to inhibit or treat the neuropsychiatric disorder.

The embodiments described above provide systems and methods for analysis of gene expression microarray data to detect potential biomarkers for a neuropsychiatric disorder and for using biomarkers detected as a result of the analysis. Application of the embodiments resulted in 177 putative SZ risk genes in DLPFC, 28 of which map to chromosomal loci linked to the disorder; delineated 6 biological processes and 12 molecular functions that may be particularly disrupted in the illness; identified 123 putative SZ biomarkers in PBCs, 6 of which had corresponding differential expression in DLPFC; verified the up-regulation of the strongest candidate SZ biomarker (SELENBP1) in PBCs; and demonstrated an altered pattern of expression of SELENBP1 protein in DLPFC in SZ. While the discussion above has focused on SZ, those of skill in the art will appreciate that the systems and methods described above may be applied to other brain regions (e.g., both implicated and nonimplicated structures, to identify ubiquitous and region-specific changes) and populations (e.g., bipolar disorder patients, to establish disease-specific changes) in order to facilitate the discovery of highly reliable and reproducible candidate risk genes and biomarkers for SZ and other neuropsychiatric disorders.

In the foregoing Detailed Description, various features are grouped together in a single embodiment for the purpose of streamlining the disclosure. This method of disclosure is not to be interpreted as reflecting an intention that the claimed embodiments have more features than are expressly recited in each claim. Thus the following claims are hereby incorporated into the Detailed Description, with each claim standing on its own as a separate embodiment.

The foregoing descriptions of specific embodiments of the present invention have been presented for purposes of illustration and description. The embodiments presented are not intended to be exhaustive or to limit the invention to the particular forms disclosed. It should be understood that one of ordinary skill in the art can recognize that the teachings of the detailed description allow for a variety of modifications and variations that are not disclosed herein but are nevertheless within the scope of the present invention. Accordingly, it is intended that the scope of the present invention be defined by the appended claims and their equivalents, rather than by the description of the embodiments.

The Abstract is provided to comply with 37 C.F.R. §1.72(b) to allow the reader to quickly ascertain the nature and gist of the technical disclosure. The Abstract is submitted with the understanding that it will not be used to limit the scope of the claims.

TABLE 1

Biological Process ontology terms overrepresented by genes differentially expressed in DLPFC in SZ

| Ontology Term | p | Gene Symbol | Gene Product | Gene Fold-Change (p) in SZ |
|---|---|---|---|---|
| ATP-Dependent Proteolysis | 0.022 | CRBN | cereblon | 1.08 (0.01660) |
| Circulation | 0.023 | LPL | lipoprotein lipase | 1.28 (0.02680) |
| | | RYR2 | ryanodine receptor 2 (cardiac) | 1.14 (0.01030) |
| | | SRI | sorcin | 1.20 (0.02480) |
| Energy Pathways | 0.007 | ACOX1 | acyl-Coenzyme A oxidase 1, palmitoyl | 1.20 (0.00480) |
| | | COX17 | COX17 homolog, cytochrome c oxidase assembly protein (yeast) | 1.10 (0.01780) |
| | | COX7C | cytochrome c oxidase subunit VIIc | 1.07 (0.04030) |
| | | GLP1R | glucagon-like peptide 1 receptor | −1.09 (0.03080) |
| | | NDUFA2 | NADH dehydrogenase (ubiquinone) 1 alpha subcomplex, 2, 8 kDa | 1.09 (0.02260) |
| | | SUCLG1 | succinate-CoA ligase, GDP-forming, alpha subunit | 1.06 (0.02870) |
| Muscle Contraction | 0.041 | CNN3 | calponin 3, acidic | 1.37 (0.01660) |
| | | RYR2 | ryanodine receptor 2 (cardiac) | 1.14 (0.01030) |
| | | SRI | sorcin | 1.20 (0.02480) |
| | | SSPN | sarcospan (Kras oncogene-associated gene) | 1.21 (0.04060) |
| Protein-Lipoylation | 0.004 | NMT1 | N-myristoyltransferase | 1.09 (0.00980) |
| Regulation of Action Potential | 0.013 | SRI | sorcin | 1.20 (0.02480) |

TABLE 2

Molecular Function ontology terms overrepresented by genes differentially expressed in DLPFC in SZ

| Ontology Term | p | Gene Symbol | Gene Product | Gene Fold-Change (p) in SZ |
|---|---|---|---|---|
| Beta-Catenin Binding | 0.041 | APC | adenomatosis polyposis coli | 1.14 (0.02510) |
| Calpain Activity | 0.009 | CAPN1 | calpain 1, (mu/l) large subunit | −1.10 (0.02210) |
| | | CAPNS1 | calpain, small subunit 1 | −1.10 (0.01740) |
| Copper Ion Transporter Activity | 0.016 | COX17 | COX17 homolog, cytochrome c oxidase assembly protein (yeast) | 1.10 (0.01780) |
| Electron Donor Activity | 0.027 | ACOX1 | acyl-Coenzyme A oxidase 1, palmitoyl | 1.20 (0.00480) |
| GABA Receptor Activity | 0.012 | GABRA2 | gamma-aminobutyric acid (GABA) A receptor, alpha 2 | 1.22 (0.01050) |
| | | GABRB1 | gamma-aminobutyric acid (GABA) A receptor, beta 1 | 1.16 (0.04360) |
| Glycylpeptide N-Tetradecanoyltransferase Activity | 0.048 | NMT1 | N-myristoyltransferase | 1.09 (0.00980) |
| MHC Protein Binding | 0.048 | TAPBP | TAP binding protein (tapasin) | −1.09 (0.02930) |
| NADH Dehydrogenase Activity | 0.019 | NDUFA2 | NADH dehydrogenase (ubiquinone) 1 alpha subcomplex, 2, 8 kDa | 1.09 (0.02260) |
| | | NDUFB5 | NADH dehydrogenase (ubiquinone) 1 beta subcomplex, 5, 16 kDa | 1.09 (0.02910) |
| | | NDUFC1 | NADH dehydrogenase (ubiquinone) 1, subcomplex unknown, 1, 6 kDa | 1.07 (0.00900) |
| Oxidoreductase Activity | 0.031 | ACOX1 | acyl-Coenzyme A oxidase 1, palmitoyl | 1.20 (0.00480) |
| | | COX7C | cytochrome c oxidase subunit VIIc | 1.07 (0.04030) |
| | | HSD17B12 | hydroxysteroid (17-beta) dehydrogenase 12 | 1.11 (0.03900) |
| | | NDUFA2 | NADH dehydrogenase (ubiquinone) 1 alpha subcomplex, 2, 8 kDa | 1.09 (0.02260) |
| | | NDUFB5 | NADH dehydrogenase (ubiquinone) 1 beta subcomplex, 5, 16 kDa | 1.09 (0.02910) |
| | | NDUFC1 | NADH dehydrogenase (ubiquinone) 1, subcomplex unknown, 1, 6 kDa | 1.07 (0.00900) |
| | | P4HA1 | procollagen-proline, 2-oxoglutarate 4-dioxygenase, alpha polypeptide I | 1.12 (0.03640) |
| Peroxisome Targeting Signal Receptor Activity | 0.031 | PEX5 | peroxisomal biogenesis factor 5 | −1.12 (0.00890) |

TABLE 2-continued

Molecular Function ontology terms overrepresented by genes differentially expressed in DLPFC in SZ

| Ontology Term | p | Gene Symbol | Gene Product | Gene Fold-Change (p) in SZ |
|---|---|---|---|---|
| Phosphoserine Phosphatase Activity | 0.009 | PSPHL | phosphoserine phosphatase-like | −2.14 (0.04420) |
| Troponin C Binding | 0.030 | CNN3 | calponin 3, acidic | 1.37 (0.01660) |

TABLE 3

Six genes differentially expressed in both DLPFC and PBCs in SZ

| Affymetrix Probe Number | Accession Number | Gene Symbol | Gene Product | Chromosomal Locus | Fold-Change (p) in SZ DLPFC | Fold-Change (p) in SZ PBCs |
|---|---|---|---|---|---|---|
| 200920_s_at | AL535380 | BTG1 | B-cell translocation gene 1, anti-proliferative | 12q22 | 1.14 (0.04020) | −1.36 (0.00008) |
| 202210_x_at | NM_019884 | GSK3A | glycogen synthase kinase 3 alpha | 19q13.2 | −1.09 (0.02490) | 1.59 (0.00044) |
| 209728_at | BC005312 | HLA-DRB1 | major histocompatibility complex, class II, DR beta 1 | 6p21.3 | −1.17 (0.04220) | NS* |
| 209312_x_at | U65585 | " | major histocompatibility complex, class II, DR beta 1 | " | NS* | −1.27 (0.00007) |
| 215193_x_at | AJ297586 | " | major histocompatibility complex, class II, DR beta 1 | " | NS* | −1.33 (0.00006) |
| 211929_at | AA527502 | HNRPA3 | heterogeneous nuclear ribonucleoprotein A3 | 2q31.2 | 1.15 (0.01410) | −2.12 (0.00004) |
| 214433_s_at | NM_003944 | SELENBP1 | selenium binding protein 1 | 1q21-q22 | 1.16 (0.04510) | 1.95 (0.00093) |
| 211784_s_at | BC006181 | SFRS1 | splicing factor, arginine/serine-rich 1 (splicing factor 2, alternate splicing factor) | 17q21.3-q22 | 1.12 (0.02460) | −1.71 (0.00005) |

*NS probe was not differentially expressed on the microarray used to profile the indicated tissue

TABLE 4

Genes differentially expressed in DLPFC in SZ

| Affymetrix Probe Number | Accession Number | Gene Symbol | Gene Product | Chromosomal Locus* | Fold-Change in SZ | p |
|---|---|---|---|---|---|---|
| 210764_s_at | AF003114 | CYR61 | cysteine-rich, angiogenic inducer, 61 | 1p31-p22 | 1.39 | 0.02990 |
| 201445_at | NM_001839 | CNN3 | calponin 3, acidic | 1p22-p21 | 1.37 | 0.01660 |
| 208859_s_at | AI650257 | ATRX | alpha thalassemia/mental retardation syndrome X-linked (RAD54 homolog, S. cerevisiae) | Xq13.1-q21.1 | 1.36 | 0.00980 |
| 215338_s_at | AI688640 | NKTR | natural killer-tumor recognition sequence | 3p23-p21 | 1.33 | 0.00280 |
| 216563_at | X80821 | ANKRD12 | ankyrin repeat domain 12 | 18p11.22 | 1.32 | 0.01470 |
| 216609_at | AF065241 | TXN | thioredoxin | 9q31 | 1.32 | 0.01980 |
| 208993_s_at | AW340788 | PPIG | peptidyl-prolyl isomerase G (cyclophilin G) | 2q31.1 | 1.30 | 0.03260 |
| 209655_s_at | AI803181 | TM4SF10 | transmembrane 4 superfamily member 10 | Xp11.4 | 1.30 | 0.01260 |
| 203548_s_at | BF672975 | LPL | lipoprotein lipase | 8p22* | 1.28 | 0.02680 |
| 217820_s_at | NM_018212 | ENAH | enabled homolog (Drosophila) | 1q42.12 | 1.28 | 0.00620 |
| 211997_x_at | NM_005324 | H3F3B | H3 histone, family 3B (H3.3B) | 17q25 | 1.26 | 0.00280 |
| 214212_x_at | AI928241 | PLEKHC1 | pleckstrin homology domain containing, family C (with FERM domain) member 1 | 14q22.1 | 1.26 | 0.04640 |
| 218930_s_at | NM_018374 | FLJ11273 | hypothetical protein FLJ11273 | 7p21.3 | 1.26 | 0.01520 |
| 202619_s_at | AI754404 | PLOD2 | procollagen-lysine, 2-oxoglutarate 5-dioxygenase (lysine hydroxylase) 2 | 3q23-q24 | 1.25 | 0.02280 |
| 202412_s_at | AW499935 | USP1 | ubiquitin specific protease 1 | 1p32.1-p31.3 | 1.23 | 0.04030 |
| 209069_s_at | BC001124 | H3F3B | H3 histone, family 3B (H3.3B) | 17q25 | 1.23 | 0.00480 |
| 207014_at | NM_000807 | GABRA2 | gamma-aminobutyric acid (GABA) A receptor, alpha 2 | 4p12 | 1.22 | 0.01050 |
| 204964_s_at | NM_005086 | SSPN | sarcospan (Kras oncogene-associated gene) | 12p11.2 | 1.21 | 0.04060 |
| 212649_at | AL079292 | DHX29 | DEAH (Asp-Glu-Ala-His) box polypeptide 29 | 5q11.2 | 1.21 | 0.04200 |
| 215450_at | W87901 | SNRPE | small nuclear ribonucleoprotein polypeptide E | 1q32 | 1.21 | 0.03350 |
| 217936_at | AW044631 | ARHGAP5 | rho GTPase activating protein 5 | 14q12* | 1.21 | 0.03890 |
| 208920_at | AV752215 | SRI | sorcin | 7q21.1 | 1.20 | 0.02480 |
| 209024_s_at | AI472757 | SYNCRIP | synaptotagmin binding, cytoplasmic RNA interacting protein | 6q14-q15 | 1.20 | 0.01850 |
| 209600_s_at | S69189 | ACOX1 | acyl-Coenzyme A oxidase 1, palmitoyl | 17q24-q25* | 1.20 | 0.00480 |
| 212044_s_at | BE737027 | RPL27A | hypothetical protein MGC10850 | 11p15 | 1.20 | 0.02780 |
| 218490_s_at | NM_018443 | ZNF302 | zinc finger protein 302 | 19q13.11 | 1.20 | 0.03440 |
| 200943_at | NM_004965 | HMGN1 | high-mobility group nucleosome binding domain 1 | 21q22.3 | 1.19 | 0.00920 |
| 222035_s_at | AI984479 | PAPOLA | poly(A) polymerase alpha | 14q32.31 | 1.19 | 0.02600 |
| 203202_at | AI950314 | HRB2 | HIV-1 rev binding protein 2 | 12q21.1 | 1.18 | 0.02550 |
| 203628_at | H05812 | IGF1R | insulin-like growth factor 1 receptor | 15q26.3 | 1.18 | 0.03650 |
| 205475_at | NM_007281 | SCRG1 | scrapie responsive protein 1 | 4q31-q32 | 1.18 | 0.02860 |
| 218859_s_at | NM_016649 | C20orf6 | chromosome 20 open reading frame 6 | 20p12.1* | 1.18 | 0.03300 |

TABLE 4-continued

Genes differentially expressed in DLPFC in SZ

| Affymetrix Probe Number | Accession Number | Gene Symbol | Gene Product | Chromosomal Locus* | Fold-Change in SZ | p |
|---|---|---|---|---|---|---|
| 201965_s_at | NM_015046 | KIAA0625 | senataxin | 9q34.13 | 1.17 | 0.01070 |
| 203549_s_at | NM_000237 | LPL | lipoprotein lipase | 8p22* | 1.17 | 0.04020 |
| 208990_s_at | AF132362 | HNRPH3 | heterogeneous nuclear ribonucleoprotein H3 (2H9) | 10q22 | 1.17 | 0.01960 |
| 210970_s_at | AF235049 | IBTK | inhibitor of Bruton agammaglobulinemia tyrosine kinase | 6q14.1 | 1.17 | 0.04700 |
| 212179_at | AW157501 | C6orf111 | chromosome 6 open reading frame 111 | 6q16.3* | 1.17 | 0.04900 |
| 212689_s_at | AA524505 | JMJD1A | jumonji domain containing 1A | 2p11.2* | 1.17 | 0.01230 |
| 214352_s_at | BF673699 | KRAS2 | v-Ki-ras2 Kirsten rat sarcoma 2 viral oncogene homolog | 12p12.1 | 1.17 | 0.00330 |
| 221960_s_at | AI189609 | RAB2 | RAB2, member RAS oncogene family | 8q12.1 | 1.17 | 0.02270 |
| 201129_at | NM_006276 | SFRS7 | splicing factor, arginine/serine-rich 7, 35 kDa | 2p22.1 | 1.16 | 0.03180 |
| 201918_at | AI927944 | FLJ10618 | hypothetical protein FLJ10618 | 3q23 | 1.16 | 0.04000 |
| 207010_at | NM_000812 | GABRB1 | gamma-aminobutyric acid (GABA) A receptor, beta 1 | 4p12 | 1.16 | 0.04360 |
| 209763_at | AL049176 | CHRDL1 | chordin-like 1 | Xq23 | 1.16 | 0.03340 |
| 212368_at | AA972711 | ZNF292 | zinc finger protein 292 | 6q15* | 1.16 | 0.04620 |
| 213792_s_at | AA485908 | INSR | insulin receptor | 19p13.3-p13.2 | 1.16 | 0.01300 |
| 214433_s_at | NM_003944 | SELENBP1 | selenium binding protein 1 | 1q21-q22 | 1.16 | 0.04510 |
| 218183_at | NM_013399 | C16orf5 | chromosome 16 open reading frame 5 | 16p13.3 | 1.16 | 0.03280 |
| 218595_s_at | NM_018072 | FLJ10359 | hypothetical protein FLJ10359 | 1q43 | 1.16 | 0.01920 |
| 202258_s_at | U50532 | PFAAP5 | phosphonoformate immuno-associated protein 5 | 13q12-q13 | 1.15 | 0.02060 |
| 211929_at | AA527502 | HNRPA3 | heterogeneous nuclear ribonucleoprotein A3 | 2q31.2 | 1.15 | 0.01410 |
| 219819_s_at | NM_014018 | MRPS28 | mitochondrial ribosomal protein S28 | 8q21.1-q21.2 | 1.15 | 0.00580 |
| 200616_s_at | BC000371 | KIAA0152 | KIAA0152 gene product | 12q24.31 | 1.14 | 0.02490 |
| 200920_s_at | AL535380 | BTG1 | B-cell translocation gene 1, anti-proliferative | 12q22 | 1.14 | 0.04020 |
| 201138_at | BG532929 | SSB | Sjogren syndrome antigen B (autoantigen La) | 2q31.1 | 1.14 | 0.00570 |
| 201637_s_at | NM_005087 | FXR1 | fragile X mental retardation, autosomal homolog 1 | 3q28 | 1.14 | 0.04690 |
| 201831_s_at | BE875592 | VDP | vesicle docking protein p115 | 4q21.1 | 1.14 | 0.02890 |
| 202324_s_at | NM_022735 | ACBD3 | acyl-Coenzyme A binding domain containing 3 | 1q42.12 | 1.14 | 0.04460 |
| 203526_s_at | M74088 | APC | adenomatosis polyposis coli | 5q21-q22 | 1.14 | 0.02510 |
| 207557_s_at | NM_001035 | RYR2 | ryanodine receptor 2 (cardiac) | 1q42.1-q43 | 1.14 | 0.01030 |
| 208663_s_at | AI652848 | TTC3 | tetratricopeptide repeat domain 3 | 21q22.2 | 1.14 | 0.04010 |
| 209049_s_at | BC001004 | PRKCBP1 | protein kinase C binding protein 1 | 20q13.12 | 1.14 | 0.03340 |
| 212332_at | BF110947 | RBL2 | retinoblastoma-like 2 (p130) | 16q12.2* | 1.14 | 0.04480 |
| 216039_at | D38503 | PMS2L1 | postmeiotic segregation increased 2-like 1 | 7q22.1 | 1.14 | 0.03510 |
| 217975_at | NM_016303 | WBP5 | WW domain binding protein 5 | Xq22.2 | 1.14 | 0.02620 |
| 200944_s_at | NM_004965 | HMGN1 | high-mobility group nucleosome binding domain 1 | 21q22.3 | 1.13 | 0.02050 |
| 201773_at | NM_015339 | ADNP | activity-dependent neuroprotector | 20q13.13 | 1.13 | 0.01290 |
| 203133_at | NM_006808 | SEC61B | Sec61 beta subunit | 9q22.32-q31.3 | 1.13 | 0.00260 |
| 208921_s_at | L12387 | SRI | sorcin | 7q21.1 | 1.13 | 0.02490 |
| 210588_x_at | L32610 | HNRPH3 | heterogeneous nuclear ribonucleoprotein H3 (2H9) | 10q22 | 1.13 | 0.04050 |
| 211930_at | AW080932 | HNRPA3 | heterogeneous nuclear ribonucleoprotein A3 | 2q31.2 | 1.13 | 0.02060 |
| 212519_at | AL518159 | UBE2E1 | ubiquitin-conjugating enzyme E2E 1 (UBC4/5 homolog, yeast) | 3p24.2* | 1.13 | 0.03680 |
| 216399_s_at | AK025663 | ZNF291 | zinc finger protein 291 | 15q24 | 1.13 | 0.00080 |
| 218435_at | NM_013238 | DNAJD1 | DnaJ (Hsp40) homolog, subfamily D, member 1 | 13q14.1 | 1.13 | 0.01580 |
| 55692_at | W22924 | ELMO2 | engulfment and cell motility 2 (ced-12 homolog, C. elegans) | 20q13 | 1.13 | 0.03050 |
| 202299_s_at | NM_006402 | HBXIP | hepatitis B virus x interacting protein | 1p13.3* | 1.12 | 0.04400 |
| 207543_s_at | NM_000917 | P4HA1 | procollagen-proline, 2-oxoglutarate 4-dioxygenase (proline 4-hydroxylase), alpha polypeptide I | 10q21.3-q23.1 | 1.12 | 0.03640 |
| 209180_at | U49245 | RABGGTB | rab geranylgeranyltransferase, beta subunit | 1p31 | 1.12 | 0.02210 |
| 211784_s_at | BC006181 | SFRS1 | splicing factor, arginine/serine-rich 1 (splicing factor 2, alternate splicing factor) | 17q21.3-q22* | 1.12 | 0.02460 |
| 211828_s_at | AF172268 | TNIK | TRAF2 and NCK interacting kinase | 3q26.2 | 1.12 | 0.04840 |
| 221613_s_at | AL136598 | ZA20D3 | zinc finger, A20 domain containing 3 | 15q25.1 | 1.12 | 0.04060 |
| 200020_at | NM_007375 | TARDBP | TAR DNA binding protein | 1p36.22 | 1.11 | 0.04070 |
| 200063_s_at | BC002398 | NPM1 | nucleophosmin (nucleolar phosphoprotein B23, numatrin) | 5q35 | 1.11 | 0.03260 |
| 202266_at | NM_016614 | TTRAP | TRAF and TNF receptor associated protein | 6p22.3-p22.1* | 1.11 | 0.04520 |
| 202301_s_at | BE396879 | FLJ11021 | similar to splicing factor, arginine/serine-rich 4 | 12q24.31 | 1.11 | 0.02420 |
| 209059_s_at | AB002282 | EDF1 | endothelial differentiation-related factor 1 | 9q34.3 | 1.11 | 0.02090 |
| 214053_at | AW772192 | ERBB4 | v-erb-a erythroblastic leukemia viral oncogene homolog 4 (avian) | 2q33.3-q34 | 1.11 | 0.04040 |
| 217869_at | NM_016142 | HSD17B12 | hydroxysteroid (17-beta) dehydrogenase 12 | 11p11.2 | 1.11 | 0.03900 |
| 222216_s_at | AK026857 | MRPL17 | mitochondrial ribosomal protein L17 | 11p15.5-p15.4 | 1.11 | 0.01650 |
| 200977_s_at | AF090891 | TAX1BP1 | tax1 (human T-cell leukemia virus type I) binding protein 1 | 7p15 | 1.10 | 0.03050 |
| 201812_s_at | NM_019059 | TOMM7 | translocase of outer mitochondrial membrane 7 homolog (yeast) | 7p15.3 | 1.10 | 0.04140 |
| 203870_at | BE856374 | USP46 | ubiquitin specific protease 46 | 4q12 | 1.10 | 0.04410 |
| 203880_at | NM_005694 | COX17 | COX17 homolog, cytochrome c oxidase assembly protein (yeast) | 3q13.33 | 1.10 | 0.01780 |
| 208726_s_at | BC000461 | EIF2S2 | eukaryotic translation initiation factor 2, subunit 2 beta, 38 kDa | 20pter-q12* | 1.10 | 0.03110 |
| 208895_s_at | BG530850 | DDX18 | DEAD (Asp-Glu-Ala-Asp) box polypeptide 18 | 2q14.1* | 1.10 | 0.04930 |
| 217724_at | AF131807 | PAI-RBP1 | PAI-1 mRNA-binding protein | 1p31-p22 | 1.10 | 0.01610 |
| 201157_s_at | AF020500 | NMT1 | N-myristoyltransferase 1 | 17q21.31 | 1.09 | 0.00980 |
| 201606_s_at | BE796924 | PWP1 | nuclear phosphoprotein similar to S. cerevisiae PWP1 | 12q23.3 | 1.09 | 0.04390 |
| 203621_at | NM_002492 | NDUFB5 | NADH dehydrogenase (ubiquinone) 1 beta subcomplex, 5, 16 kDa | 3q26.33 | 1.09 | 0.02910 |
| 209224_s_at | BC003674 | NDUFA2 | NADH dehydrogenase (ubiquinone) 1 alpha subcomplex, 2, 8 kDa | 5q31* | 1.09 | 0.02260 |
| 217898_at | NM_020154 | C15orf24 | chromosome 15 open reading frame 24 | 15q14 | 1.09 | 0.01910 |
| 217907_at | NM_014161 | MRPL18 | mitochondrial ribosomal protein L18 | 6q25.3 | 1.09 | 0.00370 |
| 218123_at | NM_017835 | C21orf59 | chromosome 21 open reading frame 59 | 21q22.1 | 1.09 | 0.00130 |

TABLE 4-continued

Genes differentially expressed in DLPFC in SZ

| Affymetrix Probe Number | Accession Number | Gene Symbol | Gene Product | Chromosomal Locus* | Fold-Change in SZ | p |
|---|---|---|---|---|---|---|
| 200728_at | BE566290 | ACTR2 | actin-related protein 2 homolog (yeast) | 2p14 | 1.08 | 0.04030 |
| 217774_s_at | NM_016404 | HSPC152 | hypothetical protein HSPC152 | 11q13.1 | 1.08 | 0.02850 |
| 217940_s_at | NM_018210 | FLJ10769 | hypothetical protein FLJ10769 | 13q34 | 1.08 | 0.01660 |
| 218142_s_at | NM_016302 | CRBN | cereblon | 3p26.2 | 1.08 | 0.01660 |
| 201134_x_at | NM_001867 | COX7C | cytochrome c oxidase subunit VIIc | 5q14 | 1.07 | 0.04030 |
| 203478_at | NM_002494 | NDUFC1 | NADH dehydrogenase (ubiquinone) 1, subcomplex unknown, 1, 6 kDa | 4q28.2-q31.1 | 1.07 | 0.00900 |
| 217491_x_at | AF042165 | COX7CP1 | cytochrome c oxidase subunit VIIc pseudogene 1 | 13q14-q21 | 1.07 | 0.03650 |
| 217874_at | NM_003849 | SUCLG1 | succinate-CoA ligase, GDP-forming, alpha subunit | 2p11.2* | 1.06 | 0.02870 |
| 200021_at | NM_005507 | CFL1 | cofilin 1 (non-muscle) | 11q13 | −1.06 | 0.04670 |
| 203929_s_at | AI056359 | MAPT | microtubule-associated protein tau | 17q21.1 | −1.07 | 0.04770 |
| 211780_x_at | BC006163 | DCTN1 | dynactin 1 (p150, glued homolog, Drosophila) | 2p13 | −1.07 | 0.03780 |
| 213867_x_at | AA809056 | ARHGEF10 | rho guanine nucleotide exchange factor (GEF) 10 | 8p23 | −1.07 | 0.02110 |
| 201864_at | NM_001493 | GDI1 | GDP dissociation inhibitor 1 | Xq28 | −1.08 | 0.02220 |
| 202508_s_at | NM_003081 | SNAP25 | synaptosomal-associated protein, 25 kDa | 20p12-p11.2* | −1.08 | 0.02980 |
| 202752_x_at | NM_012244 | SLC7A8 | solute carrier family 7 (cationic amino acid transporter, y+ system), member 8 | 14q11.2* | −1.08 | 0.01790 |
| 203103_s_at | NM_014502 | PRP19 | PRP19/PSO4 homolog (S. cerevisiae) | 11q12.2 | −1.08 | 0.01750 |
| 206213_at | NM_003394 | WNT10B | wingless-type MMTV integration site family, member 10B | 12q13 | −1.08 | 0.04540 |
| 214626_s_at | AK026548 | GANAB | glucosidase, alpha; neutral AB | 11q12.3 | −1.08 | 0.01490 |
| 221966_at | AA813194 | RH98400 | chromosome 11 hypothetical protein ORF4 | 11cen-q22.3* | −1.08 | 0.01840 |
| 35265_at | U31501 | FXR2 | fragile X mental retardation, autosomal homolog 2 | 17p13.1 | −1.08 | 0.00660 |
| 200758_s_at | AI361227 | NFE2L1 | nuclear factor (erythroid-derived 2)-like 1 | 17q21.3 | −1.09 | 0.01890 |
| 202210_x_at | NM_019884 | GSK3A | glycogen synthase kinase 3 alpha | 19q13.2 | −1.09 | 0.02490 |
| 202801_at | NM_002730 | PRKACA | protein kinase, cAMP-dependent, catalytic, alpha | 19q13.1 | −1.09 | 0.04400 |
| 203906_at | AI652645 | IQSEC1 | IQ motif and Sec7 domain 1 | 3p25.2* | −1.09 | 0.04350 |
| 205331_s_at | NM_016606 | C5orf19 | chromosome 5 open reading frame 19 | 5q31* | −1.09 | 0.01970 |
| 207366_at | NM_002251 | KCNS1 | potassium voltage-gated channel, delayed-rectifier, subfamily S, member 1 | 20q12 | −1.09 | 0.04360 |
| 208390_s_at | U01104 | GLP1R | glucagon-like peptide 1 receptor | 6p21* | −1.09 | 0.03080 |
| 208829_at | AF029750 | TAPBP | TAP binding protein (tapasin) | 6p21.3* | −1.09 | 0.02930 |
| 214354_x_at | T91506 | SFTPB | surfactant, pulmonary-associated protein B | 2p12-p11.2* | −1.09 | 0.02470 |
| 219521_at | NM_018644 | B3GAT1 | beta-1,3-glucuronyltransferase 1 (glucuronosyltransferase P) | 11q25 | −1.09 | 0.04350 |
| 220465_at | NM_024988 | FLJ12355 | hypothetical protein FLJ12355 | 19q13.11 | −1.09 | 0.00970 |
| 221591_at | AB049127 | MARK4 | MAP/microtubule affinity-regulating kinase 4 | 19q13.3 | −1.09 | 0.02540 |
| 200001_at | NM_001749 | CAPNS1 | calpain, small subunit 1 | 19q13.12 | −1.10 | 0.01740 |
| 200639_s_at | NM_003406 | YWHAZ | tyrosine 3-monooxygenase/tryptophan 5-monooxygenase activation protein, zeta polypeptide | 8q23.1 | −1.10 | 0.03720 |
| 200752_s_at | NM_005186 | CAPN1 | calpain 1, (mu/I) large subunit | 11q13 | −1.10 | 0.02210 |
| 202676_x_at | NM_006712 | FASTK | FAST kinase | 7q35 | −1.10 | 0.04340 |
| 202806_at | NM_004395 | DBN1 | drebrin 1 | 5q35.3 | −1.10 | 0.02130 |
| 203618_at | AB023167 | FAIM2 | Fas apoptotic inhibitory molecule 2 | 12q13 | −1.10 | 0.02870 |
| 204947_at | NM_005225 | E2F1 | E2F transcription factor 1 | 20q11.2 | −1.10 | 0.00300 |
| 204980_at | NM_004898 | CLOCK | clock homolog (mouse) | 4q12 | −1.10 | 0.04370 |
| 209229_s_at | BC002799 | KIAA1115 | KIAA1115 | 19q13.42 | −1.10 | 0.01650 |
| 210975_x_at | BC000377 | FASTK | FAST kinase | 7q35 | −1.10 | 0.03390 |
| 211677_x_at | AF062733 | IGSF4B | immunoglobulin superfamily, member 4B | 1q21.2-q22 | −1.10 | 0.02190 |
| 214903_at | AF070580 | FLJ42519 | CDNA FLJ42519 fis, clone BRACE3000787 | 1q32 | −1.10 | 0.03390 |
| 217419_x_at | AK021586 | AGRN | agrin | 1p36.33 | −1.10 | 0.03320 |
| 219400_at | NM_003632 | CNTNAP1 | contactin associated protein 1 | 17q21 | −1.10 | 0.03850 |
| 221901_at | BF516072 | KIAA1644 | KIAA1644 protein | 22q13 | −1.10 | 0.03390 |
| 47560_at | AI525402 | LPHN1 | latrophilin 1 | 19p13.2 | −1.10 | 0.02260 |
| 203151_at | AW296788 | MAP1A | microtubule-associated protein 1A | 15q13-qter | −1.11 | 0.02680 |
| 203831_at | NM_014925 | KIAA1002 | KIAA1002 protein | 12q13.3 | −1.11 | 0.00700 |
| 205325_at | NM_014759 | PHYHIP | phytanoyl-CoA hydroxylase interacting protein | 8p21.3* | −1.11 | 0.04680 |
| 208823_s_at | BE787860 | PCTK1 | PCTAIRE protein kinase 1 | Xp11.3-p11.23 | −1.11 | 0.03640 |
| 211240_x_at | AB002382 | CTNND1 | catenin (cadherin-associated protein), delta 1 | 11q11 | −1.11 | 0.01540 |
| 217766_s_at | NM_014313 | SMP1 | small membrane protein 1 | 1p36.11 | −1.11 | 0.01340 |
| 220974_x_at | NM_030971 | BA108L7.2 | similar to rat tricarboxylate carrier-like protein | 10q24.32 | −1.11 | 0.00260 |
| 221535_at | AL136897 | FLJ11301 | hypothetical protein FLJ11301 | 3q29 | −1.11 | 0.00450 |
| 203244_at | NM_000319 | PEX5 | peroxisomal biogenesis factor 5 | 12p13.3 | −1.12 | 0.00890 |
| 203264_s_at | NM_015185 | ARHGEF9 | Cdc42 guanine nucleotide exchange factor (GEF) 9 | Xq11.2 | −1.12 | 0.03980 |
| 207629_s_at | NM_004723 | ARHGEF2 | rho/rac guanine nucleotide exchange factor (GEF) 2 | 1q21-q22 | −1.12 | 0.04820 |
| 209435_s_at | BC000265 | ARHGEF2 | rho/rac guanine nucleotide exchange factor (GEF) | 1q21-q22 | −1.12 | 0.00820 |
| 217637_at | R25692 | Unknown | full length insert cDNA clone ZE05A03 | 20q13.1 | −1.12 | 0.04500 |
| 212252_at | AA181179 | CAMKK2 | calcium/calmodulin-dependent protein kinase kinase 2, beta | 12q24.2 | −1.13 | 0.03980 |
| 212699_at | BE222801 | SCAMP5 | secretory carrier membrane protein 5 | 15q23 | −1.13 | 0.04090 |
| 204893_s_at | NM_004799 | ZFYVE9 | zinc finger, FYVE domain containing 9 | 1p32.3 | −1.14 | 0.04040 |
| 211934_x_at | W87689 | GANAB | glucosidase, alpha; neutral AB | 11q12.3 | −1.14 | 0.01130 |
| 212285_s_at | AW008051 | AGRN | agrin | 1p36.33 | −1.14 | 0.00740 |
| 217991_x_at | NM_018070 | SSBP3 | single stranded DNA binding protein 3 | 1p32.3 | −1.14 | 0.01450 |
| 218952_at | NM_013271 | PCSK1N | proprotein convertase subtilisin/kexin type 1 inhibitor | Xp11.23 | −1.14 | 0.03060 |
| 205508_at | NM_001037 | SCN1B | sodium channel, voltage-gated, type I, beta | 19q13.1 | −1.15 | 0.00770 |

TABLE 4-continued

Genes differentially expressed in DLPFC in SZ

| Affymetrix Probe Number | Accession Number | Gene Symbol | Gene Product | Chromosomal Locus* | Fold-Change in SZ | p |
|---|---|---|---|---|---|---|
| 209728_at | BC005312 | HLA-DRB1 | major histocompatibility complex, class II, DR beta 1 | 6p21.3* | −1.17 | 0.04220 |
| 219724_s_at | NM_014796 | KIAA0748 | KIAA0748 gene product | 12q13.2 | −1.21 | 0.00310 |
| 203337_x_at | NM_004763 | ITGB1BP1 | integrin beta 1 binding protein 1 | 2p25.2 | −1.29 | 0.01930 |
| 217427_s_at | X75296 | HIRA | HIR histone cell cycle regulation defective homolog A (*S. cerevisiae*) | 22q11.2* | −1.32 | 0.00940 |
| 205048_s_at | NM_003832 | PSPHL | phosphoserine phosphatase-like | 7q11.2 | −2.14 | 0.04420 |

*Implicated in SZ by meta-analysis of genome-wide linkage studies (22)

TABLE 5

Genes differentially expressed in PBCs in SZ

| Affymetrix Probe Number | Accession Number | Gene Symbol | Gene Product | Chromosomal Locus | Fold-Change in SZ | p |
|---|---|---|---|---|---|---|
| 210746_s_at | M30646 | EPB42 | erythrocyte membrane protein band 4.2 | 15q15-q21 | 2.35 | 0.00053 |
| 211560_s_at | AF130113 | ALAS2 | aminolevulinate, delta-, synthase 2 (sideroblastic/hypochromic anemia) | Xp11.21 | 2.34 | 0.00111 |
| 213524_s_at | NM_015714 | G0S2 | putative lymphocyte G0/G1 switch gene | 1q32.2-q41 | 2.28 | 0.00146 |
| 219672_at | NM_016633 | ERAF | erythroid associated factor | 16p11.2 | 2.13 | 0.00029 |
| 209890_at | AF065389 | TM4SF9 | transmembrane 4 superfamily member 9 | 4q23 | 2.12 | 0.00203 |
| 203691_at | NM_002638 | PI3 | protease inhibitor 3, skin-derived (SKALP) | 20q12-q13 | 2.05 | 0.00001 |
| 211781_x_at | BC006164 | Unknown | hypothetical protein MGC13219 | Unknown | 2.04 | 0.00007 |
| 219630_at | NM_005764 | MAP17 | membrane-associated protein 17 | 1p33 | 2.01 | 0.00011 |
| 205950_s_at | NM_001738 | CA1 | carbonic anhydrase I | 8q13-q22.1 | 1.99 | 0.00049 |
| 210395_x_at | AF116676 | MYL4 | myosin, light polypeptide 4, alkali; atrial, embryonic | 17q21-qter | 1.99 | 0.00003 |
| 204466_s_at | BG260394 | SNCA | synuclein, alpha (non A4 component of amyloid precursor) | 4q21 | 1.95 | 0.00119 |
| 214433_s_at | NM_003944 | SELENBP1 | selenium binding protein 1 | 1q21-q22 | 1.95 | 0.00093 |
| 201178_at | NM_012179 | FBXO7 | F-box protein 7 | 22q12-q13 | 1.91 | 0.00025 |
| 211475_s_at | AF116273 | BAG1 | BCL2-associated athanogene | 9p12 | 1.89 | 0.00175 |
| 206834_at | NM_000519 | HBD | hemoglobin, delta | 11p15.5 | 1.86 | 0.00132 |
| 210088_x_at | M36172 | MYL4 | myosin, light polypeptide 4, alkali; atrial, embryonic | 17q21-qter | 1.84 | 0.00004 |
| 202219_at | NM_005629 | SLC6A8 | solute carrier family 6 (neurotransmitter transporter, creatine), member 8 | Xq28 | 1.83 | 0.00026 |
| 218872_at | NM_017899 | TSC | hypothetical protein FLJ20607 | 12q24.22 | 1.83 | 0.00019 |
| 201161_s_at | NM_003651 | CSDA | cold shock domain protein A | 12p13.1 | 1.81 | 0.00240 |
| 202387_at | NM_004323 | BAG1 | BCL2-associated athanogene | 9p12 | 1.80 | 0.00130 |
| 204419_x_at | NM_000184 | HBG2 | hemoglobin, gamma G | 11p15.5 | 1.80 | 0.00501 |
| 204467_s_at | NM_000345 | SNCA | synuclein, alpha (non A4 component of amyloid precursor) | 4q21 | 1.80 | 0.00256 |
| 216054_x_at | X58851 | MYL4 | myosin, light polypeptide 4, alkali; atrial, embryonic | 17q21-qter | 1.79 | 0.00002 |
| 204187_at | NM_006877 | GMPR | guanosine monophosphate reductase | 6p23 | 1.77 | 0.00011 |
| 220757_s_at | NM_025241 | UBXD1 | UBX domain containing 1 | 19p13 | 1.77 | 0.00434 |
| 202947_s_at | NM_002101 | GYPC | glycophorin C (Gerbich blood group) | 2q14-q21 | 1.73 | 0.00752 |
| 202201_at | NM_000713 | BLVRB | biliverdin reductase B (flavin reductase (NADPH)) | 19q13.1-q13.2 | 1.70 | 0.00390 |
| 204848_s_at | NM_000559 | HBG1 | hemoglobin, gamma A | 11p15.5 | 1.69 | 0.00779 |
| 202859_x_at | NM_000584 | IL8 | interleukin 8 | 4q13-q21 | 1.68 | 0.00347 |
| 207827_x_at | L36675 | SNCA | synuclein, alpha (non A4 component of amyloid precursor) | 4q21 | 1.68 | 0.00061 |
| 211546_x_at | L36674 | SNCA | synuclein, alpha (non A4 component of amyloid precursor) | 4q21 | 1.68 | 0.00008 |
| 200844_s_at | BE869583 | PRDX6 | peroxiredoxin 6 | 1q25.1 | 1.66 | 0.00251 |
| 202364_at | NM_005962 | MXI1 | MAX interactor 1 | 10q24-q25 | 1.66 | 0.00005 |
| 204505_s_at | NM_001978 | EPB49 | erythrocyte membrane protein band 4.9 (dematin) | 8p21.1 | 1.65 | 0.00214 |
| 214273_x_at | AV704353 | C16orf35 | chromosome 16 open reading frame 35 | 16p13.3 | 1.65 | 0.00131 |
| 217748_at | NM_015999 | ADIPOR1 | adiponectin receptor 1 | 1p36.13-q41 | 1.65 | 0.00138 |
| 220807_at | NM_005331 | HBQ1 | hemoglobin, theta 1 | 16p13.3 | 1.62 | 0.00439 |
| 206207_at | NM_001828 | CLC | Charcot-Leyden crystal protein | 19q13.1 | 1.61 | 0.00009 |
| 210638_s_at | AF176704 | FBXO9 | F-box protein 9 | 6p12.3-p11.2 | 1.61 | 0.00001 |
| 202074_at | NM_021980 | OPTN | optineurin | 10p13 | 1.60 | 0.00048 |
| 202210_x_at | NM_019884 | GSK3A | glycogen synthase kinase 3 alpha | 19q13.2 | 1.59 | 0.00044 |
| 205592_at | X77737 | SLC4A1 | solute carrier family 4, anion exchanger, member 1 (erythrocyte membrane protein band 3, Diego blood group) | 17q21-q22 | 1.59 | 0.00400 |
| 221479_s_at | AF060922 | BNIP3L | BCL2/adenovirus E1B 19 kDa interacting protein 3-like | 8p21 | 1.56 | 0.00543 |
| 201052_s_at | BG029917 | PSMF1 | proteasome (prosome, macropain) inhibitor subunit 1 (PI31) | 20p13 | 1.55 | 0.00652 |
| 40850_at | L37033 | FKBP8 | FK506 binding protein 8, 38 kDa | 19p12 | 1.52 | 0.00462 |
| 217882_at | NM_018447 | LOC55831 | 30 kDa protein | 3p25.3 | 1.51 | 0.00863 |
| 205863_at | NM_005621 | S100A12 | S100 calcium binding protein A12 (calgranulin C) | 1q21 | 1.50 | 0.00018 |
| 208949_a_at | BC001120 | LGALS3 | lectin, galactoside-binding, soluble, 3 (galectin 3) | 14q21-q22 | 1.47 | 0.00157 |
| 215499_at | AA780381 | MAP2K3 | mitogen-activated protein kinase kinase 3 | 17q11.2 | 1.47 | 0.00001 |
| 203966_s_at | NM_021003 | PPM1A | protein phosphatase 1A (formerly 2C), magnesium-dependent, alpha isoform | 14q23.1 | 1.46 | 0.00013 |
| 210183_x_at | AF112222 | PNN | pinin, desmosome associated protein | 14q21.1 | 1.45 | 0.00028 |

TABLE 5-continued

Genes differentially expressed in PBCs in SZ

| Affymetrix Probe Number | Accession Number | Gene Symbol | Gene Product | Chromosomal Locus | Fold-Change in SZ | p |
|---|---|---|---|---|---|---|
| 204018_x_at | NM_000558 | HBA1 | hemoglobin, alpha 1 | 16p13.3 | 1.43 | 0.00001 |
| 211699_x_at | AF349571 | HBA1 | hemoglobin, alpha 1 | 16p13.3 | 1.43 | 0.00003 |
| 217756_x_at | NM_005770 | SERF2 | small EDRK-rich factor 2 | 15q15.3 | 1.43 | 0.00132 |
| 200633_at | NM_018955 | UBB | ubiquitin B | 17p12-p11.2 | 1.41 | 0.00031 |
| 217414_x_at | V00489 | HBA2 | hemoglobin, alpha 2 | 16p13.3 | 1.40 | 0.00008 |
| 201285_at | NM_013446 | MKRN1 | makorin, ring finger protein, 1 | 7q34 | 1.39 | 0.00044 |
| 209116_x_at | M25079 | HBB | hemoglobin, beta | 11p15.5 | 1.38 | 0.00002 |
| 211745_x_at | BC005931 | HBA2 | hemoglobin, alpha 2 | 16p13.3 | 1.38 | 0.00005 |
| 217232_x_at | AF059180 | HBB | hemoglobin, beta | 11p15.5 | 1.36 | 0.00005 |
| 214271_x_at | AA281332 | RPL12 | ribosomal protein L12 | 9q34 | 1.35 | 0.00001 |
| 209458_x_at | AF105974 | HBA1 | hemoglobin, alpha 1 | 16p13.3 | 1.34 | 0.00012 |
| 221700_s_at | AF348700 | UBA52 | ubiquitin A-52 residue ribosomal protein fusion product 1 | 19p13.1-p12 | 1.33 | 0.00005 |
| 214290_s_at | AI313324 | H2AFO | H2A histone family, member O | 1p36.13-q24.1 | 1.30 | 0.00089 |
| 211696_x_at | AF349114 | HBB | hemoglobin, beta | 11p15.5 | 1.29 | 0.00002 |
| 217977_at | NM_016332 | SEPX1 | selenoprotein X, 1 | 16p13.3 | 1.29 | 0.00265 |
| 214414_x_at | T50399 | HBA1 | hemoglobin, alpha 1 | 16p13.3 | 1.26 | 0.00076 |
| 211911_x_at | L07950 | HLA-B | major histocompatibility complex, class I, B | 6p21.3 | −1.21 | 0.00038 |
| 209619_at | K01144 | CD74 | CD74 antigen (invariant polypeptide of major histocompatibility complex, class II antigen-associated) | 5q32 | −1.24 | 0.00010 |
| 200871_s_at | NM_002778 | PSAP | prosaposin (variant Gaucher disease and variant metachromatic leukodystrophy) | 10q21-q22 | −1.27 | 0.00003 |
| 209312_x_at | U65585 | HLA-DRB1 | major histocompatibility complex, class II, DR beta 1 | 6p21.3* | −1.27 | 0.00007 |
| 200904_at | X56841 | HLA-E | major histocompatibility complex, class I, E | 6p21.3 | −1.28 | 0.00003 |
| 208980_s_at | M26880 | UBC | ubiquitin C | 12q24.3 | −1.28 | 0.00037 |
| 212363_x_at | AU145192 | ACTG1 | actin, gamma 1 | 17q25 | −1.30 | 0.00045 |
| 205237_at | NM_002003 | FCN1 | ficolin (collagen/fibrinogen domain containing) 1 | 9q34 | −1.33 | 0.00055 |
| 215193_x_at | AJ297586 | HLA-DRB1 | major histocompatibility complex, class II, DR beta 1 | 6p21.3 | −1.33 | 0.00006 |
| 201368_at | U07802 | ZFP36L2 | zinc finger protein 36, C3H type-like 2 | 2p22.3-p21 | −1.35 | 0.00018 |
| 200634_at | NM_005022 | PFN1 | profilin 1 | 17p13.3 | −1.36 | 0.00001 |
| 200866_s_at | M32221 | PSAP | prosaposin (variant Gaucher disease and variant metachromatic leukodystrophy) | 10q21-q22 | −1.36 | 0.00015 |
| 200920_s_at | AL535380 | BTG1 | B-cell translocation gene 1, anti-proliferative | 12q22 | −1.36 | 0.00008 |
| 200772_x_at | BF686442 | PTMA | prothymosin, alpha (gene sequence 28) | 2q35-q36 | −1.37 | 0.00032 |
| 208438_s_at | NM_005248 | FGR | Gardner-Rasheed feline sarcoma viral (v-fgr) oncogene homolog | 1p36.2-p36.1 | −1.38 | 0.00001 |
| 219505_at | NM_017424 | CECR1 | cat eye syndrome chromosome region, candidate 1 | 22q11.2 | −1.38 | 0.00001 |
| 200742_s_at | BG231932 | CLN2 | ceroid-lipofuscinosis, neuronal 2, late infantile (Jansky-Bielschowsky disease) | 11p15 | −1.41 | 0.00001 |
| 200743_s_at | NM_000391 | CLN2 | ceroid-lipofuscinosis, neuronal 2, late infantile (Jansky-Bielschowsky disease) | 11p15 | −1.41 | 0.00001 |
| 205898_at | U20350 | CX3CR1 | chemokine (C-X3-C motif) receptor 1 isoform, 1, cardiac muscle | 3p21 | −1.41 | 0.00002 |
| 213738_s_at | AI587323 | ATP5A1 | ATP synthase, H+ transporting, mitochondrial F1 complex, alpha subunit, | 18q12-q21 | −1.44 | 0.00008 |
| 211991_s_at | M27487 | HLA-DPA1 | major histocompatibility complex, class II, DP alpha 1 | 6p21.3 | −1.48 | 0.00002 |
| 212192_at | AI718937 | KCTD12 | potassium channel tetramerisation domain containing 12 | 13q22.3 | −1.49 | 0.00005 |
| 207419_s_at | NM_002872 | RAC2 | ras-related C3 botulinum toxin substrate 2 (rho family, small GTP binding protein Rac2) | 22q13.1 | −1.51 | 0.00092 |
| 211921_x_at | AF348514 | PTMA | prothymosin, alpha (gene sequence 28) | 2q35-q36 | −1.52 | 0.00002 |
| 204912_at | NM_001558 | IL10RA | interleukin 10 receptor, alpha | 11q23 | −1.54 | 0.00006 |
| 208743_s_at | BC001359 | YWHAB | tyrosine 3-monooxygenase/tryptophan 5-monooxygenase activation protein, beta polypeptide | 20q13.1 | −1.54 | 0.00003 |
| 205292_s_at | NM_002137 | HNRPA2B1 | heterogeneous nuclear ribonucleoprotein A2/B1 | 7p15 | −1.59 | 0.00001 |
| 203037_s_at | NM_014751 | MTSS1 | metastasis suppressor 1 | 8p22 | −1.60 | 0.00002 |
| 203104_at | NM_005211 | CSF1R | colony stimulating factor 1 receptor, formerly McDonough feline sarcoma viral (v-fms) oncogene homolog | 5q33-q35 | −1.63 | 0.00001 |
| 56256_at | AA150165 | SIDT2 | SID1 transmembrane family, member 2 | 11q23.3 | −1.63 | 0.00001 |
| 201393_s_at | NM_000876 | IGF2R | insulin-like growth factor 2 receptor | 6q26 | −1.66 | 0.00015 |
| 211784_s_at | BC006181 | SFRS1 | splicing factor, arginine/serine-rich 1 (splicing factor 2, alternate splicing factor) | 17q21.3-q22 | −1.71 | 0.00005 |
| 214617_at | AI445650 | PRF1 | perforin 1 (pore forming protein) | 10q22 | −1.71 | 0.00001 |
| 203741_s_at | NM_001114 | ADCY7 | adenylate cyclase 7 | 16q12-q13 | −1.73 | 0.00002 |
| 213475_s_at | AC002310 | ITGAL | integrin, alpha L (antigen CD11A (p180), lymphocyte function-associated antigen 1; alpha polypeptide) | 16p11.2 | −1.73 | 0.00001 |
| 208988_at | BE675843 | FBOXL11 | F-box and leucine-rich repeat protein 11 | 11q13.2 | −1.75 | 0.00001 |
| 213872_at | BE465032 | C6orf62 | chromosome 6 open reading frame 62 | 6p22.2 | −1.75 | 0.00014 |
| 218396_at | NM_017684 | VPS13C | vacuolar protein sorting 13C (yeast) | 15q22.2 | −1.79 | 0.00002 |
| 209007_s_at | AF267856 | NPD014 | NPD014 protein | 1p36.13-p35.1 | −1.80 | 0.00001 |
| 201218_at | N23018 | CTBP2 | C-terminal binding protein 2 | 10q26.13 | −1.86 | 0.00003 |
| 203113_s_at | NM_001960 | EEF1D | eukaryotic translation elongation factor 1 delta (guanine nucleotide exchange protein) | 8q24.3 | −1.86 | 0.00118 |
| 202663_at | AI005043 | WASPIP | Wiskott-Aldrich syndrome protein interacting protein | 2q31.1 | −1.89 | 0.00001 |
| 215646_s_at | R94644 | CSPG2 | chondroitin sulfate proteoglycan 2 (versican) | 5q14.3 | −1.91 | 0.00008 |
| 202230_s_at | NM_006387 | CHERP | calcium homeostasis endoplasmic reticulum protein | 19p13.1 | −1.94 | 0.00001 |

TABLE 5-continued

Genes differentially expressed in PBCs in SZ

| Affymetrix Probe Number | Accession Number | Gene Symbol | Gene Product | Chromosomal Locus | Fold-Change in SZ | p |
|---|---|---|---|---|---|---|
| 201798_s_at | NM_013451 | FER1L3 | fer-1-like 3, myoferlin (*C. elegans*) | 10q24 | −1.95 | 0.00001 |
| 212070_at | AL554008 | GPR56 | G protein-coupled receptor 56 | 16q13 | −2.02 | 0.00001 |
| 204516_at | BG390306 | ATXN7 | ataxin 7 | 3p21.1-p12 | −2.05 | 0.00001 |
| 214683_s_at | AI251890 | CLK1 | CDC-like kinase 1 | 2q33 | −2.07 | 0.00002 |
| 201088_at | NM_002266 | KPNA2 | karyopherin alpha 2 (RAG cohort 1, importin alpha 1) | 17q23.1-q23.3 | −2.08 | 0.00002 |
| 208810_at | AF080569 | DNAJB6 | DnaJ (Hsp40) homolog, subfamily B, member 6 | 7q36.3 | −2.09 | 0.00001 |
| 211929_at | AA527502 | HNRPA3 | heterogeneous nuclear ribonucleoprotein A3 | 2q31.2 | −2.12 | 0.00004 |
| 213906_at | AW592266 | MYBL1 | v-myb myeloblastosis viral oncogene homolog (avian)-like 1 | 8q22 | −2.22 | 0.00020 |
| 203132_at | NM_000321 | RB1 | retinoblastoma 1 (including osteosarcoma) | 13q14.2 | −2.46 | 0.00005 |
| 209006_s_at | AF247168 | NPD014 | NPD014 protein | 1p36.13-p35.1 | −2.67 | 0.00001 |
| 221768_at | AV705803 | SFPQ | splicing factor proline/glutamine rich (polypyrimidine tract binding protein associated) | 1p34.3 | −2.73 | 0.00051 |
| 202817_s_at | NM_005637 | SS18 | synovial sarcoma translocation, chromosome 18 | 18q11.2 | −7.24 | 0.00002 |

The invention claimed is:

1. A method to diagnose schizophrenia, comprising:
   detecting an amount or level of selenium binding protein expression in a sample of cells from a human suspected of having schizophrenia;
   determining the amount or level of selenium binding protein expression in said cells; and
   comparing said amount or level to that in a corresponding sample from a human not having schizophrenia, wherein an increase in selenium binding protein expression is indicative of schizophrenia.

2. The method of claim 1, wherein the sample is blood.

3. The method of claim 1 wherein the cells are peripheral blood cells.

4. The method of claim 1 wherein detecting an amount or level of selenium binding protein expression comprises measuring protein.

5. The method of claim 1 wherein detecting an amount or level of selenium binding protein expression comprises measuring RNA.

6. The method of claim 1 wherein the selenium binding protein is selenium binding protein-1 (SELENBP-1).

7. The method of claim 1 wherein detecting an amount or level of selenium binding protein expression in a sample of cells comprises detecting the amount or level of selenium binding protein-1 expression in blood.

* * * * *